United States Patent [19]
Rhodes et al.

[11] Patent Number: 5,759,515
[45] Date of Patent: *Jun. 2, 1998

[54] POLYVALENT PEPTIDE PHARMACEUTICAL APPLICATIONS

[75] Inventors: Buck A. Rhodes, Albuquerque, N. Mex.; Paul O. Zamora, Bonn, Germany; Richard J. Freer, Richmond, Va.; Shubh D. Sharma, Albuquerque, N. Mex.

[73] Assignee: Rhomed Incorporated, Albuquerque, N. Mex.

[*] Notice: The term of this patent shall not extend beyond the expiration date of Pat. No. 5,700,444.

[21] Appl. No.: 269,929

[22] Filed: Jun. 30, 1994

Related U.S. Application Data

[63] Continuation-in-part of Ser. No. 87,219, Jul. 2, 1993, Pat. No. 5,700,444, which is a continuation-in-part of Ser. No. 840,077, Feb. 20, 1992, Pat. No. 5,443,816, which is a continuation-in-part of Ser. No. 565,275, Aug. 8, 1990, Pat. No. 5,102,990, which is a continuation-in-part of Ser. No. 391,474, Aug. 9, 1989, Pat. No. 5,078,985.

[51] Int. Cl.$^6$ .................... A61K 51/00; A61M 36/14
[52] U.S. Cl. .................. 424/1.69; 424/1.11; 424/1.65; 530/300; 530/329; 530/330
[58] Field of Search ................. 424/1.69, 1.11, 424/1.65, 9.1; 530/324, 300, 329, 325, 326, 327, 330, 334, 338; 534/7, 10–16

[56] References Cited

U.S. PATENT DOCUMENTS

| | | | |
|---|---|---|---|
| 4,424,200 | 1/1984 | Crockford et al. | 424/1.1 |
| 4,427,646 | 1/1984 | Olexa et al. | 424/1.1 |
| 4,479,930 | 10/1984 | Hnatowich | 424/1.1 |
| 4,668,503 | 5/1987 | Hnatowich | 424/1.1 |
| 4,732,864 | 3/1988 | Tolman | 436/547 |
| 4,904,642 | 2/1990 | Coy et al. | 514/11 |
| 4,986,979 | 1/1991 | Morgan, Jr. et al. | 424/1.1 |
| 5,039,662 | 8/1991 | Schasteen | 514/17 |
| 5,061,641 | 10/1991 | Shochat et al. | 436/545 |
| 5,078,985 | 1/1992 | Rhodes | 530/391.5 |
| 5,091,514 | 2/1992 | Fritzberg et al. | 534/14 |
| 5,092,885 | 3/1992 | Yamada et al. | 623/11 |
| 5,102,990 | 4/1992 | Rhodes | 530/391.5 |
| 5,128,119 | 7/1992 | Griffiths | 424/1.1 |
| 5,162,505 | 11/1992 | Dean et al. | 530/391.5 |
| 5,169,933 | 12/1992 | Anderson et al. | 530/391.3 |
| 5,225,180 | 7/1993 | Dean et al. | 424/1.1 |
| 5,225,530 | 7/1993 | Bernardi et al. | 530/324 |
| 5,229,490 | 7/1993 | Tam | 530/324 |
| 5,236,903 | 8/1993 | Saiki et al. | 514/12 |
| 5,371,184 | 12/1994 | Rajagopalan et al. | 530/324 |
| 5,443,816 | 8/1995 | Zamora et al. | 424/1.69 |
| 5,508,020 | 4/1996 | Dean et al. | 424/1.69 |

FOREIGN PATENT DOCUMENTS

| | | | |
|---|---|---|---|
| 2016235 | 9/1990 | Canada | 530/7.06 |
| 0196669 | 4/1986 | European Pat. Off. | C07K 17/06 |
| 0250013 | 5/1987 | European Pat. Off. | C07F 13/00 |
| WO 92/13572 | 2/1992 | WIPO | A61K 49/02 |
| WO93/23085 | 11/1993 | WIPO | A61K 49/02 |
| WO93/25244 | 12/1993 | WIPO | A61K 49/02 |

OTHER PUBLICATIONS

Bard, D.R., et al., "BisMSH–DTPA: A Potential Imaging Agent for Malignant Melanoma," *Ann NY Acad Sci.* 680, pp. 451–453 (1993).

Bard, D.R., et al., "A Chelating Derivative of α–Melanocyte Stimulating Hormone as a Potential Imaging Agent for Malignant Melanoma," *Br J Cancer*, vol. 62 pp. 919–922 (1990).

Cox, P.H., et al., "Technetium Labelled Somatostatin A Potential Agent for In Vivo Tumour Localization," *7th Int'l Sympos on Radiopharm.*, p. 16 (1991) Abstract.

Fischman, A.J., et al., "A Ticket to Ride: Peptide Radiopharmaceuticals," *J Nucl Med*, vol. 34, No. 12, pp. 2253–2263 (1993).

Hynes, R.O., "Inegrins: Versatility, Modulation, and Signaling in Cell Adhesion," *Cell*, vol. 69, pp. 11–25 (1992).

Ill, C.R., et al., "Adhesion of Platelets to Laminin in the Absence of Activation," *J Cell Bio*, vol. 99, pp. 2140–2145, (1984).

Khaw, B.A., et al., "Technetium–99m Labeling of Antibodies to Cardiac Myosin Fab and to Human Fibrinogen," *J Nucl Med*, vol. 23, No. 11, pp. 1011–1019 (1982).

Knight, L.C., et al., "Thrombus Imaging with TC–99m Synthetic Peptides Reactive with Activated Platelets," *J Nucl Med*, vol. 31, No. 5, No. 209 Abstract (May 1990).

Kondo, M., et al., "Studies of Dimeric fMLF with High Chemotactic Activities," *Peptides: Chemistry and Biology*, JA Smith and JE Rivier, eds., ESCOM, Leiden, pp. 425–426 (1992).

Kraus, J, et al., "Cyclic Tetrameric Clusters of Chemotactic Peptides as Superactive Activators of Lysozyme Release from Human Meutrophils," *Bilchem and Biophy Res Comm*, vol. 124, No. 3, pp. 939–944 (1984).

Sonnenberg, A., et al., "Isolation of ∂6β1 Integrins from Platelets and Adherent Cells by Chromatography on Mouse Laminin Fragment E8 and Human Laminin Pepsin Fragment," *Exp Cell Res*, vol. 197, pp. 234–244 (1991).

Tandon, N.N., et al., "Interaction of Human Platelets with Laminin and Identification of 67 kDa Laminin Receptor on Platelets," *Biochem J*, vol. 2724, pp. 535–542 (1991).

(List continued on next page.)

*Primary Examiner*—John Kight
*Assistant Examiner*—Dameron Jones
*Attorney, Agent, or Firm*—Darby & Darby

[57] ABSTRACT

High affinity linked, branched or linear repeat peptides containing two or more biological-function domains and at least one medically useful metal ion-binding domain are labeled with medically useful metal ions for use in a variety of diseases and pathologic conditions, including diagnosis and treatment of diseases. Such peptides include high affinity chemotactic peptides containing a biological-function domain which includes at least two linked N-formyl-MLF (SEQ. ID NO. 2) sequences and high affinity repeat and branched peptides containing two or more YIGSR (SEQ. ID NO. 1) sequences.

11 Claims, No Drawings

OTHER PUBLICATIONS

Swanson, D., et al., "In-111 Laminin Peptide Fragments for Malignant Tumor Detection," *J Nucl Med*, 34, 231P Abstract (1993).

Wraight, E.P., et al., "The Use of Chelating Derivative of Alpha Melanocyte Stimulating Hormone for the Clinical Imaging of Malignant Melanoma," *Brit J Rad*, vol. 65, pp. 112–118 (1992).

Yamada, K.M., "Adhesive Recognition Sequences," *J Biol Chem*, vol. 266, No. 20, pp. 12809–12812 (1992).

Pimm, M.V., et al., "In labelling of a branched polypeptide drug carrier with a poly(L-lysine) backbone," Int'l J. Pharm., vol. 79 (1992), pp. 77–80.

Nakai et al. "A Synthetic Antagonist to Laminin Inhibits the Formation of Osteolytic Metastases by Human Melanoma Cells in Nude Mice". Cancer Research, vol. 52, pp. 5395–5399, Oct. 1, 1992.

Saiki et al. "Antimetastatic effects of synthetic polypeptides containing repeated structures of the cell adhesive Arg–Gly–Asp (RGD) and Tyr–Ile–Gly–Ser–Arg, (YIGSR) sequences". British Journal of Cancer, vol. 60, pp. 722–728, (1989).

Saiki et al 'The inhibition of murine lung metastatis by synthetic poly peptides [poly(arg–gly–asp)] and [(poly (tyr–i/e–gly–ser–arg)] with a core sequence of cell adhesion molecules". British Journal of Cancer, vol. 59, pp. 194–197, (1989).

POLYVALENT PEPTIDE PHARMACEUTICAL APPLICATIONS

CROSS-REFERENCE TO RELATED APPLICATIONS

This application is a continuation-in-part application of U.S. patent application Ser. No. 08/087,219, U.S. Pat. No. 5,700,444, filed Jul. 2, 1993, entitled *Chemotactic Peptide Pharmaceutical Applications*; which in turn is a continuation-in-part application of U.S. patent application Ser. No. 07/840,077, filed Feb. 20, 1992, now U.S. Pat. No. 5,443,816, entitled *Peptide-Metal Ion Pharmaceutical Preparation and Method*; which in turn is a continuation-in-part application of U.S. patent application Ser. No. 07/565,275, filed Aug. 8, 1990 now U.S. Pat. No. 5,102,990, entitled *Direct Radiolabeling of Antibodies and Other Proteins with Technetium or Rhenium*; which in turn is a continuation-in-part application of U.S. patent application Ser. No. 07/391,474, filed Aug. 9, 1989 now U.S. Pat. No. 5,078,985, entitled *Radiolabeling Antibodies and Other Proteins with Technetium or Rhienium by Regulated Reduction*; and is related to U.S. patent application Ser. No. 07/864,470, entitled *Direct Radiolabeling of Substrates Containing Monosulfides or Disulfide Bonds with Radionuclides*; U.S. patent application Ser. No. 07/816,477, entitled *Direct Labeling of Antibodies and Other Proteins with Metal Ions*; U.S. patent application Ser. No. 07/998,820, entitled *IKVAV Peptide Radiopharmaceutical Applications*; and U.S. patent application Ser. No. 07/998,910, entitled *YIGSR Peptide Radiopharmaceutical Aplications*; the teachings of all of the foregoing which are incorporated herein by reference.

BACKGROUND OF THE INVENTION

1. Field of the Invention (Technical Field)

The present invention relates to polyvalent peptides, primarily linked, branched or linear repeat peptides, with two or more biological-function domains, and one or more metal ion-binding function domains, for use in peptide-based metal ion-labeled compositions for use as pharmaceuticals, and methods of labeling with radiometals, paramagnetic metals and other medically useful metal ions, and further providing for use of medically useful metal ion-labeled polyvalent peptides for detection and treatment of disease.

2. Background Art

Peptide-Based Radiopharmaceuticals.

The use of biologically active peptides, which are peptides that bind to specific cell surface receptors or that in other ways modify cellular function, has received some consideration as radiopharmaceuticals. Biospecific imaging and radiotherapy agents started with large proteins, such as antibodies, and have evolved to antibody fragments, antigen binding domain fragments and small biologically active peptides. The smaller size of biologically active peptides confers pharmacokinetic properties, such as higher target-to-non-target ratios and faster blood clearance, which are desirable for some diagnostic imaging applications. However, use of biologically active peptides is not without limitations. Generally, biologically active peptides have a significantly lower binding affinity to receptor sites than comparable antibodies. Mechanisms of clearance may be so rapid that insufficient targeting is achieved. Because of the relatively small size of biologically active peptides, chemical modification by introduction of labeling groups can result in drastic biodistribution and pharmacokinetic changes.

Several peptide-based radiopharmaceutical products are in development, including use of somatostatin as an imaging agent. Receptors for somatostatin are expressed on a variety of human tumors and their metastases. Using somatostatin analogs, $^{123}$I-labeled Tyr-3-octreotide and $^{111}$In-DTPA-octreotide imaging agents have been developed, and research is being conducted on a variety of $^{99m}$Tc-labeled somatostatin analogs, including direct-labeled somatostatin analogs. Research work is also being conducted on use of chemotactic peptides for diagnostic imaging of sites of infection or inflammation. Both $^{111}$In- and $^{99m}$Tc-labeled chemiotactic peptides have been developed, and used in limited studies. Melanotropin imaging agents have been reported for imaging melanoma tumors which express melanotropin receptors, using $^{111}$In-DTPA-melanotropin. Other biologically active peptide sequences are being considered as potential radiopharmaceutical products.

Peptides may be radiolabeled by any of a variety of means. Biologically active peptides for radiopharnaceuticals include that disclosed by Olexa S. A., Knight L. C. and Budzynski A. Z., U.S. Pat. No. 4,427,646, *Use of Radiolabeled Peptide Derived From Crosslinked Fibrin to Locate Thrombi In Vivo*, in which iodination is discussed as a means of radiolabeling. Peptides may be directly radioiodinated, through electrophilic substitution at reactive aromatic amino acids. Iodination may also be accomplished via prelabeled reagents, in which the reagent is iodinated and purified, and then linked to the peptide. In Morgan C. A. Jr and Anderson D. C., U.S. Pat. No. 4,986,979, *Imaging Tissue Sites of Inflammation*, use of chelates and direct iodination is disclosed.

The utility of DTPA and EDTA chelates covalently coupled to polypeptides and similar substances are well known in the art. Hnatowich, D. J., U.S. Pat. Nos. 4,479,930 and 4,668,503. DTPA has been used as a bifunctional chelating agent for radiolabeling a variety of peptides with $^{111}$In, including α-melanocyte-simulating hormone for imaging melanoma, chemotactic peptides for infection imaging, laminin fragments for targeting tumor-associated laminin receptors and atrial natriuretic peptide for imaging atrial natriuretic receptors in the kidney.

Techlnetium-99m is a preferred isotope for diagnostic imaging, due to its low cost, ready availability, excellent imaging properties and high specific activities. Two approaches have been described for radiolabeling proteins and peptides with $^{99m}$Tc: direct labeling and bifunctional chelates. In Dean R. T., Lister-James J and Buttram S, U.S. Pat. No. 5,225,180, *Technetium-99m Labeled Somatostatin-Derived Peptides for Imaging*, direct labeling of somatostatin through reduction of native disulfide bonds resulting from cross-linked cysteine residues is disclosed. In U.S. patent application Ser. No. 07/816,477, entitled *Direct Labeling of Antibodies and Other Proteins with Metal Ions*, and U.S. patent application Ser. No. 07/840,077, entitled *Peptide-Metal Ion Pharmaceutical Preparation and Method*, a variety of methods of direct labeling of peptides through sulfur-, oxygen- and nitrogen-containing amino acid sequences available for binding are disclosed.

A variety of high affinity chelates to bind $^{99m}$Tc to specific sites on peptides have been developed. In one approach, the bifunctional reagent is first labeled with $^{99m}$Tc, and then conjugated to the peptide. However, multiple species can result, and post-labeling purification is generally required. In another approach, a chelating agent is covalently attached to the peptide prior to radiolabeling. In Tolman G. L., U.S. Pat. No. 4,732,864, *Trace-Labeled Conjugates of Metallothlionein and Target-Seeking Biologically Active Molecules*, the use of metallothionein or metallothionein fragments conjugated to a biologically active molecule, including peptides, is disclosed. Other clielates which have been employed include a variety of $N_2S_2$ and $N_3S$ ligands, DTPA, and 6-hydrazinonicotinate groups.

Chemotactic Peptides.

One class of peptide which has received attention as a potential radiopharmaceutical are chemotactic peptides, which are known to bind to neutrophils through discrete receptors and to result in regulation and/or activation of various neutrophil receptors and stimulation of integrin-mediated adhesion. A sequence used frequently as a chemotactic sequence is N-formyl-Met-Leu-Phe (N-formyl-MLF). Canadian Patent Application 2,016,235, Labeled Chemotactic Peptides to Image Focal Sites of Infection or Inflammation, teaches a method of detecting a site of infection or inflammation, and a method for treating such infection or inflammation, by administration of a labeled or therapeutically-conjugated chemotactic peptide. In this application, the chemotactic peptides are chemically conjugated to DTPA and subsequently labeled with $^{111}$In.

Specific types of neutrophil cell surface molecules which are upregulated by chemotactic peptides include CD14, CD15, CR3, and CD18. This, in turn, results in attachment of the neutrophils to activated endothelium and subsequent diapedesis to sites of infection. Blood-borne chemotactic peptides, therefore, stimulate circulating neutrophils to localize to sites of infection (e.g. sites of activated endothelium).

There is no simple, direct-labeled, radiopharmaceutical in general clinical use for the specific imaging of infections and inflammations. $^{67}$Ga-citrate and $^{111}$In-oxine-labeled white blood cells are currently used clinically, but both present significant limitations. $^{67}$Ga-citrate is not specific in its uptake into infections, and the radionuclide is not monoenergetic, has a relatively long half-life, and requires delayed imaging due to slow blood clearance. Use of $^{111}$In-oxine-labeled white blood cells has a much higher abscess specificity, however the labeling method is technically demanding and requires isolation of the patient's cells. Other methods, including the use of radiolabeled, non-specific, human gamma globulin, and $^{99m}$Tc-anti-granulocyte antibodies, have not come into routine clinical use. Potential drawbacks of radiolabeled antibodies include high manufacturing costs and the formation of human anti-mouse antibodies.

YIGSR-Containing Peptides.

Under homeostatic conditions, platelets circulate as disc shaped cells that do not interact with other circulating blood cells or vascular endothelium. Upon injury, platelets rapidly a) attach to dysfunctional or detached endothelial cells and b) migrate and localize to the underlying basement membrane and tissues. Differences in platelet response, correlating to the degree of injury, are due in part to differences in the vessel wall composition of the molecules to which the platelets adhere. For example, type I and III collagens, which are typically associated with smooth muscle cells, promote platelet adhesion, aggregation, and release. In contrast, types IV and V collagens, typically associated with the endothelium, facilitate platelet adhesion but do not generally cause platelet activation.

Platelet-mediated thrombosis is a major pathogenetic mechanism in thrombogenesis and reocclusion after successful thrombolytic therapy, and consequently platelets are frequently used as vehicles for localization of thrombi. Additionally, suppression of platelet aggregation is a frequent target for prevention of blood vessel occlusion or reocclusion. There are a number of clinical conditions in which there are platelet accumulations; these include venous thrombosis, arterial thrombosis, left ventricular thrombosis, pulmonary embolism, inflammatory response secondary to myocardial infarction, endocarditis, bypass graft occlusion, aneurysms, prosthetic arterial graft platelet accumulation or occlusion, cerebral embolism or hemorrhage, traumatic injury with hemorrhage, gastrointestinal hemorrhage, and thrombosis secondary to catheters and other implanted devices.

Knight et al. (Knight L. C., Radcliffe R., Kollman M., Dasika V., Wikander R., Mauer A. H., Rodwell J. D., and Alvarez V.: Thrombus imaging with Tc-99m synthetic peptides reactive with activated platelets. J Nucl Med 31(1990) 757 (abstract)) have reported on the use of $^{99m}$Tc-synthetic peptide-metallothionein complexes which bind to the platelet glycoprotein IIb/IIIa complex to image fresh thrombi in jugular veins. However, peptides which target the glycoprotein IIb/IIIa complex are known to adversely affect platelet aggregation, and consequently a radiopharmaceutical based on such an approach would be expected to have severe dose limitations.

Laminin is a basement membrane glycoprotein ($M_r$=900, 000) which has various biological activities including promoting cell attachment, growth, and differentiation. A typical laminin molecule consists of three polypeptide chains, A (440 kd), B1 (200 kd), and B2 (220 kd), linked by disulfide bonds to form an asymmetric cross-structure. Multiple, distinct adhesive sequences in laminin appear to mediate specific biological functions, and bind to distinct cell surface receptors (Hynes R. O.: Integrins: versatility, modulation, and signaling in cell adhesion, Cell 69(1992) 11–25; Yamada K. M.: Adhesive recognition sequences, J Biol Chem 266 (1992) 2809–2812).

Integrin-type receptors on platelets (glycoprotein Ib, the glycoprotein IIb/IIIa complex and glycoprotein IV) have been identified as the major adhesion receptors in platelets, but these glycoproteins do not appear to play a role in the interaction of platelets with the intact laminin molecule (Tandon N. N., Holland E. A., Kralisz U, Kleinman H. K., Robey F. A., and Jamieson G. A.: Interaction of human platelets with laminin and identification of the 67 kDa laminin receptor on platelets, Biochem J 274(1991) 535–542). However, platelets do bind to laminin peptide fragments via these receptors (Sonnenberg A, Gehlsen K. R., Aumailley M, and Timpl R: Isolation of α6β1 integrins from platelets and adherent cells by affinity chromatography on mouse laminin fragment E8 and human laminin pepsin fragment, Exp Cell Res 197(1991) 234–244), suggesting that normally these sites in laminin are cryptic for platelets. One non-integrin platelet receptor for laminin is a 67 kDa receptor which binds to laminin-derived peptide sequences containing Tyr-Ile-Gly-Ser-Arg (YIGSR)(SEQ. ID NO. 1)(Tandon et al., supra). This platelet receptor appears to play an important role in the interaction of platelets with the intact laminin molecule. Platelet adherence to laminin via this receptor does not in itself result in platelet activation (Ill CR, Engvall E, and Ruoslahti E: Adhesion of platelets to laminin in the absence of activation. J Cell Biol 99(1984) 2140–2145).

Peptides containing the YIGSR (SEQ. ID No. 1) peptide sequence have been proposed as anti-metastatic agents. Schasteen C. S., U.S. Pat. No. 5,039,662, Peptide with Anti-Metastatic Activity; Yamada Y, Graf J. O., Iwamoto Y, Rober F, Kleinman H. K., Sasaki M. and Martin G. R., U.S. Pat. No. 5,092,885, Peptides with Laminin Activity; and Saiki I., Nishi N., Azuma I., Tokura S., U.S. Pat. No. 5,236,903 *Polypeptide Comprising Repeated Cell-Adhesive Core Sequences*. These patents involve longer sequences containing the YIGSR (SEQ. ID No. 1) peptide sequence, acylated YIGSR (SEQ. ID No. 1) peptide sequences, cyclic YIGSR (SEQ. ID No. 1) sequences, and repeated YIGSR (SEQ. ID No. 1) linear sequences.

Linked, Branched and Repeat Sequence Peptides.

Use of peptide constructs as immunogens or antigens, such as for vaccines, has been explored by several researchers. Tam J. P., U.S. Pat. No. 5,229,490, *Multiple Antigen Peptide System*, and Bernardi A., Bonelli F., Pessi A., Verdini A. S., U.S. Pat. No. 5,225,530, *Polypeptide Useful for the Preparation of Antimalarial Vaccines and of Diagnostic Kits for the Detection of Malarial Affections*. Tam describes a method of constructing antigens in which peptide antigen sequences are covalently bonded to polyamide branches through peptide bonds, forming a denritic homopolymer. Tills branched construct can be made employing branched lysine structures, resulting in two-, four- or eight-branched constructs, in which the peptide antigen is connected to the lysine residue via a glycine linker. In Bernardi et al a peptide immunogen is described which incorporates a repeated four peptide sequence.

Peptide analogs, such as tetrameric chemotactic peptide analogs, have been shown to have extremely high affinities. Kraus J. L., Diapola A., Belleau B.: Cyclo tetrameric clusters of chemotactic peptides as superactive activators of lysozyme release from human neutrophils. *Biochem Biophsy Res Commun* 124 (1984) 945–949. In these studies, a tetramer was formed by synthesizing N-formyl-Met-Leu-Phe amide sequences bridged to tetraazacycloalkanes through 6 carbon spacers.

Radiolabeled peptide constructs, with two binding sequences coupled to DTPA, have also been reported. A dimer $^{111}$In-DTPA-labeled laminin sequence was prepared for tumor imaging, in which the diner was formed by reacting a peptide sequence containing a single YIGSR (SEQ. ID NO. 1) with DTPA dianhydride, yielding a dimer represented by the formula DTPA-(GYIGSR-NH$_2$)$_2$ (derived from SEQ. ID NO. 1). In preliminary studies the dimer was more potent than a peptide with a single YIGSR (SEQ. ID NO. 1) sequence. Swanson D., Epperly M., Brown M. L. et al: In-111 laminin peptide fragments for malignant tumor detection. *J Nucl Med* 34 (1993) 231 P (Abstract). Use of a repeat YIGSR (SEQ. ID NO. 1) sequence, employed for therapeutic purposes, is described in Saiki I. et al, supra. A dimer of a melanotropin analog linked to $^{111}$In-DTPA in a similar fashion has also been reported as an imaging agent for metastatic melanoma. Wraight E. P., Bard D. R., Maughan T. S. et al, *Br J Radiology* 65 (1992) 112–118, and Bard D. R., Wraight E. P., Knight C. G.: BisMSH-DTPA: a potential imaging agent for malignant melanoma. *Ann NY Acad Sci* 680 (1993) 451–453.

SUMMARY OF THE INVENTION (DISCLOSURE OF THE INVENTION)

In accordance with the present invention, a high affinity peptide-based pharmaceutical composition suitable for administration to a patient is provided, which pharmaceutical composition includes at least two linear repeat, linked, or branched amino acid sequence biological-function domains, and one or more medically useful amino acid sequence metal ion-binding domains. This peptide-based pharmaceutical composition, which includes at least two linear repeat, linked or branched amino acid sequence biological-function domains and one or more medically useful metal ion-binding domains, can be selected from the group which includes $(R_1)-[Y_1]_n-(R_2)$, $(R_1)-[Y_1-(R_2)-Y_1]_n-(R_3)$, and $(R_1)-[Y_1-(R_2)-Y_2]_n-(R_3)$ wherein, the medically useful metal ion-binding domain is selected from one of the group consisting of $[Y_1]_n$, $[Y_1-(R_2)-Y_1]_n$ and $[Y_1-(R_2)-Y_2]_n$ in which n is a number between 1 and about 6 and $Y_1$ and $Y_2$ are amino acids comprising a sulfur, nitrogen or oxygen which is available for binding to metal ions or can be made available for binding to metal ions;

the linear repeat, linked, or branched amino acid sequence biological-function domains include at least one of the group consisting of $R_1$, $R_2$ and $R_3$; and those portions of $R_1$, $R_2$ and $R_3$ which do not include the biological-function domain each include an amino acid sequence containing from 0 to about 20 amino acids.

The peptide-based pharmaceutical composition includes compositions in which the medically useful metal ion-binding domain includes at least one amino acid sequence selected from the group including cysteine, cystine, histidine, penicillamine, methionine, lysine, arginine, aspartic acid, glutamic acid and tyrosine. The metal ion-binding domain can be selected from the group consisting of $[Cys]_n$, $[Cys-(R_2)-Cys]_n$, $[Cys-(R_2)-Pen]_n$, $[His-(R_2)-Cys]_n$, $[His-(R_2)-Pen]_n$, $[His]_n$ and $[His-(R_2)-His]_n$ wherein, n is a number between 1 and about 6; and $R_2$ is an amino acid sequence containing from 1 to about 20 amino acids.

In another embodiment, the medically useful metal ion-binding domain of the peptide-based pharmaceutical composition can be selected from the group consisting of the following:

B—NH—CH$_2$ ⏋
B—NH—CH$_2$ ⏌ ,

B-Dap(B)-COOH,

B-J-J-J,

B-J-Cys,

J-Cys(S-aminoethyl), and

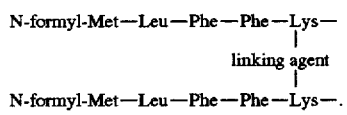
Cys(S-aminoethyl)-Cys(S-aminoethyl)

wherein,
- B is selected from the group consisting of Pro, 3-(2-Thiazolyl)alanine, 2-Thiophenecarboxylic acid, and 2-Thiopheneacetic acid; "Dap" is 2,3 diaminopropionic acid here and throughout this patent application;
- J is selected from the group consisting of Gly and Ala residues; and
- amino acids are L- or D-amino acids, or combinations thereof.

The peptide-based pharmaceutical composition includes compositions in which the linked biological-function domains includes

```
N-formyl-Met—Leu—Phe—Phe—Lys—
                              |
                         linking agent
                              |
N-formyl-Met—Leu—Phe—Phe—Lys—.
```

The peptide-based pharmaceutical composition also includes compositions in which the repeat biological-function domains includes (Tyr-Ile-Gly-Ser-Arg-U)$_n$ (derived from SEQ. ID NO. 1),
wherein,
- n is a number between 1 and about 8; and
- U is an amino acid sequence containing from 1 to about 20 amino acids.

Similarly, the peptide-based pharmaceutical composition includes compositions in which the branched biological-function domains comprise (Tyr-Ile-Gly-Ser-Arg-X)$_n$ (derived from SEQ. ID NO. 1),
wherein,
- n is a number between 1 and about 8; and
- X is an amino acid sequence containing from 1 to about 20 amino acids which form a polyamide branch through peptide bonds joined to a central core molecule.

The peptide-based pharmaceutical composition can also include a stannous metal ion labeling agent, and may further also include a medically useful metal ion. The medically useful metal ion can be a radionuclide, including isotopes of technetium, rhenium, indium, gold, silver, mercury and copper.

In another embodiment, a method of performing a diagnostic procedure in a patient is provided, which method includes the steps of a) preparing a medically useful metal ion-labeled peptide which includes a peptide sequence including at least two linked N-formyl-Met-Leu-Phe (SEQ. ID NO. 2) sequences and a medically useful metal ion, and b) administering the medically useful metal ion-labeled peptide to the patient in a sufficient amount to accumulate at a target locus, and c) determining the locus of accumulation of the medically useful metal ion labeled peptide in the patient. The diagnostic procedure can include detection of sites of neutrophil accumulation. Detection of sites of neutrophil accumulation can be used in the diagnosis of infections and sterile inflammations.

In another embodiment, a method of performing a diagnostic procedure in a patient is provided, which includes the steps of a) preparing a medically useful metal ion-labeled peptide comprising a peptide sequence comprising at least two linear repeated, linked, or branched Tyr-Ile-Gly-Ser-Arg (SEQ. ID NO. 1) sequences and a medically useful metal ion, b) administering the medically useful metal ion-labeled peptide to the patient in a sufficient amount to accumulate at a target locus; and c) determining the locus of accumulation of the medically useful metal ion labeled peptide in the patient. The diagnostic procedure can include detection of sites of platelet accumulation. Detection of sites of platelet accumulation can be used in the diagnosis of thrombosis, pulmonary embolism, inflammatory response secondary to myocardial infarction, endocarditis, bypass graft occlusion, aneurysms, prosthetic arterial graft platelet accumulation, prosthetic arterial graft platelet occlusion, cerebral embolism, cerebral hemorrhage, traumatic injury with hemorrhage, gastrointestinal hemorrhage, and thrombosis secondary to catheters and other implanted devices. The diagnostic procedure can also include detection of carcinomas, including primary carcinomas and metastatic carcinomas.

Accordingly, it is an object of the present invention to provide for pharmaceutically useful peptides comprising two or more biological-function domains, and a medically useful metal ion-binding domain.

Another object of the present invention is to provide for high affinity peptide-based radiopharmaceutical agents, both diagnostic and therapeutic, by use of peptides comprising two or more repeat, linked or branched biological-function domains, each biological-function domain including at least one biological binding sequence, and one or more medically useful metal ion-binding domains.

It is a further object of the present invention to provide a means whereby metal ion-binding domains can be directly synthesized or genetically introduced into a peptide with repeat, linked or branched biological function domains, thereby allowing labeling without the necessity of conjugation to bifunctional chelators.

Another object of the present invention is to provide a method for performing a diagnostic procedure by administration of a metal ion-labeled peptide composed of two or more repeat, linked or branched biological-function domains, with each domain including at least one biological binding sequence, and one or more medically useful metal ion-binding domains.

Another object of the present invention is to provide a method and product which permit labeling to be accomplished by the end user using a single vial, containing a peptide with two or more repeat, linked or branched biological-function domains including at least one biological binding sequence, one or more medically useful metal ion-binding domains, and a metal ion labeling agent, which method requires only a single step to accomplish labeling, being the introduction of the medically useful metal ion.

Another object of the present invention is to provide for pharmaceutically useful chemotactic peptides comprising two or more linked biological-function domains, each incorporating N-formyl-MLF (SEQ. ID NO. 2) sequences, and one or more medically useful metal ion-binding domain.

Another object of the invention is to provide a means to substantially increase the affinity of chemotactic peptides for their receptor by linking two or ore N-formyl-MLF (SEQ. ID NO. 2) sequences.

Another object of the present invention is to provide a method for the direct labeling of chemotactic peptides incorporating two or more linked N-formyl-MLF (SEQ. ID NO. 2) sequences and amino acid sequences containing amino acids with sulfur, nitrogen or oxygen which is available or can be made available for binding metal ions, such as cysteine, histidine or penicillamine, or some combination thereof.

It is a further object of the present invention to provide a method to label chemotactic peptides incorporating two or more linked N-formyl-MLF (SEQ. ID NO. 2) sequences with medically useful metal ions while retaining high biological activity subsequent to the labeling process.

Another object of the present invention is to provide for pharmaceutically useful peptides comprising two or more repeat, linked or branched biological-function domains each containing the sequence YIGSR (SEQ. ID NO. 1) and a linked metal ion.

It is a further object of the present invention to provide a means whereby thrombosis and other diseases and lesions characterized by concentrations of platelets can be diagnosed and treated through use of a peptide containing repeat, linked or branched YIGSR (SEQ. ID NO. 1) sequences.

It is a further object of the present invention to provide a means whereby one or more metal ion-binding domains can be directly synthesized or genetically introduced into a peptide comprising two or more repeat, linked, or branched biological-function domains containing the sequence YIGSR (SEQ. ID NO. 1), thereby allowing labeling without the necessity of conjugation to bifunctional chelators.

It is a further object of the present invention to provide a method for performing a diagnostic procedure by administration of a metal ion-labeled peptide composed of two or more linked, repeat or branched biological-function domains containing the sequence YIGSR (SEQ. ID NO. 1) and one or more metal ion-binding domains.

Other objects, advantages and novel features, and further scope of applicability of the present invention will be set forth in part in the detailed description to follow and in part will become apparent to those skilled in the art upon examination of the following, or may be learned by practice of the invention. The objects and advantages of the invention may be realized and attained by means of the instrumentalities and combinations particularly pointed out in the appended claims.

DETAILED DESCRIPTION OF THE PREFERRED EMBODIMENTS OF THE INVENTION (BEST MODES FOR CARRYING OUT THE INVENTION)

Using the methods of this invention, peptides with two or more linear repeated, linked or branched biological-function domains, with each domain including a biologically active peptide sequence, and a linked radiometal, provide materials useful for in vivo diagnostic and therapeutic applications. When labeled with gamma emitting radioisotopes, such as Technetium-99m, such peptides can be used for diagnostic imaging of specific cell surface receptor associated diseases or pathologies. When labeled with alpha or beta emitting radioisotopes, such as Rhenium-186 or Rhenium-188, such peptides can be used for therapy of specific cell surface receptor associated diseases.

The terms "bind," "binding," "complex," and "complexing," as used throughout the specification and claims, are intended to cover all types of physical and chemical binding, reactions, complexing, attraction, chelating and the like.

The peptides of the invention can be:

a) naturally-occurring, b) produced by chemical synthesis, c) produced by recombinant DNA technology, d) produced by biochemical or enzymatic fragmentation of larger molecules, e) produced by methods resulting from a combination of a–d, or f) produced by any other means for producing peptides.

By employing chemical synthesis, the preferred means of production, it is possible to introduce various amino acids which do not naturally occur along the chain, modify the N- or C-terminus, and the like, thereby providing for greater lifetime of the peptide, improved stability and formulation, resistance to protease degradation, and the like. The term "peptide" as used throughout the specification and claims is intended to include any structure comprised of two or more amino acids. For the most part, the peptides of this invention comprise fewer than 100 amino acids, and preferably fewer than 60 amino acids, and most preferably ranging from about 20 to 40 amino acids.

By "linear repeat" biological-function domains are meant linear peptides in which the biologically active peptide sequence is repeated two or more times, preferably with one or more intervening or spacer amino acids between the biologically active peptide sequences, and most preferably when the intervening amino acids include glycine. An example of a linear repeat biological-function domain is the sequence YIGSRGGYIGSRGGYIGSR (derived from SEQ. ID NO. 1), in which YIGSR (SEQ. ID NO. 1) is the biological-function domain, and GG are intervening or spacer amino acids.

By "linked" biological-function domains are meant two or more linear peptides, each containing at least one biologically active peptide sequence, which are linked through an amino acid group. A variety of linkers may be employed, such as succinate and other dicarboxylic acids, diamine compounds, and other homo- and lietero-bifunctional crosslinking agents.

By "branched" biological-function domains are means peptide constructs, containing two or more linear sequences, each containing at least one biologically active peptide sequence, which are branched or linked to a central core molecule. These include linear sequences bound to the functional group of a dendritic core molecule, as is described in Tam J. P., U.S. Pat. No. 5,229,490, *Multiple Antigen Peptide System*, the teachings of which are incorporated herein.

The biological-function domain of the peptide is defined in the specification and claims as a sequence of one or more amino acids which constitute a biologically active peptide sequence, exhibiting binding to a biological receptor found on cells, tissues, organs or fluids. The peptides may or may not transmit a signal to the cells, tissues or other materials associated with the biological receptor after binding. The biological-function domain also includes a sequence of one or more amino acids which exhibit binding to a biological receptor found on other peptides, enzymes, antibodies or similar proteinaceous compositions which may themselves exhibit binding to another biological receptor.

The product resulting from the methods set forth herein can be used for both medical applications and veterinary applications. Typically, the product is used in humans, but may also be used in other mammals. The term "patient" is intended to denote a mammalian individual, and is so used throughout the specification and in the claims. The primary applications of the invention involve human patients, but the invention may be applied to laboratory, farm, zoo, wildlife, pet or sport animals.

The metal ion-binding domain of the peptide is defined in the pecification and claims as a sequence of one or more amino acids, or modified amino acids, containing sulfur, nitrogen or oxygen atoms which are available for binding or can be made available for binding to metal ions. Sulfur-containing amino acids include primarily cysteine (Cys), cystine (Cys-Cys) and penicillamine (Pen), although methionine (Met), and other amino acids, may also be used. Useful nitrogen-containing amino acids include primarily histidine (His), but under certain conditions lysine (Lys) and arginine (Arg), which have $pK_a$ values of 10.0 and 12.0, and other amino acids, may also be employed. In addition, the terminal amino group of peptides may also be employed. Useful oxygen-containing amino acids include aspartic acid (Asp), glutamic acid (Glu), tyrosine (Tyr), serine (Ser) and threonine (Thr), as well as the terminal carboxyl group of peptides and other moieties. The amino acid sequences most usefully employed will include one or more Cys, one or more His, or a combination of Cys and His. Pen, which is an analogue of Cys, may be directly substituted for any given Cys. Cys may be present in the peptide as a disulfide in the form of cystine. The metal ion-binding domain may employ L-amino acids, or one or more of the amino acids may be substituted by D-amino acids (D-stereoisomer). The metal ion-binding domains may occur once or multiple times in any given peptide, and may occur in any combination. The metal ion-binding domain and the biological-function domain may overlap.

The metal binding sequences as found in the peptides of this invention may be stabilized by the addition of a positively-charged transition metal ion, such as Zn, Cu, Sn, Co, or Ni, and the like, selected to have a low order of binding strength. Through a replacement reaction, the transition metal ion replaces the H ion of the thiolate, imidazole or carboxyl group. The divalent ions of zinc and tin are thought to be particularly attractive. Some transition metals can simultaneously be used to reduce disulfide bridges and stabilize the metal binding sequences, such as Sn (II), which is particularly useful with cystine formations. In any case, the transition metals are weakly associated with the peptide.

The positively-charged transition metal ions are introduced to the peptide in an aqueous solution containing an appropriate buffer. The buffer may consist of dicarboxylic acids (tartrate, phthalate, citrate), amino acids (glycine, diglycine, tri-glycine), borate, glucoheptonate, or the like. The buffer components may also be used as stabilizers for metal ions and/or as transfer agents or ligands for radionuclides, such as $^{99m}$Tc. For radiolabeling in acidic conditions, typically 10 mM tartrate and 40 mM phthalate at pH values of about 5 to about 7 are used. For radiolabeling in basic conditions, typically 10 mM glycine at pH values of about 8 to about 10 are used. The buffer may also contain a number of excipients and/or stabilizers including NaCl, inositol, glucoheptonate, and the like.

The peptide of this invention is complexed with a medically useful metal ion. The medically useful metal ion may be radioactive and generate gamma rays, beta particles, or positrons which are converted into gamma rays upon collision with electrons. Alternatively, the medically useful metal ion may be paramagnetic or supramagnetic. The medically useful metal ion may used in diagnostic imaging procedures including gamma scintigraphy, specific photon emission computerized tomography, positron emission tomography or magnetic resonance imaging.

Particularly useful metal ions can be found in the group consisting of elements 26-30 (Fe, Co, Ni, Cu, Zn), 33-34 (As, Se), 42-50 (Mo, Tc, Ru, Rh, Pd, Ag, Cd, In, Sn) and 75-85 (Re, Os, Ir, Pt, Au, Hg, Tl, Pb, Bi, Po, At). Isotopes of the elements Tc and Re are particularly applicable for use in diagnostic imaging and radiotherapy. The isotope $^{99m}$Tc is particularly applicable for use in diagnostic imaging. The isotopes $^{186}$Re and $^{188}$Re are particularly applicable for use in radiotherapy. Other radionuclides with diagnostic or therapeutic applications include $^{62}$Cu, $^{64}$Cu, $^{67}$Cu, $^{97}$Ru, $^{105}$Rh, $^{109}$Pd, $^{186}$Re, $^{188}$Re, $^{198}$Au, $^{199}$Au, $^{203}$Pb, $^{211}$Pb and $^{212}$Bi. The type of medically useful metal ion depends on the specific medical application. The medically-useful metal ion is selected to have a higher order of binding than the positively charged-transition metal ion used to stabilize the metal binding sequences. In the case of $^{99m}$Tc, the peptides are reacted with sodium pertechnetate which has been treated with a reducing agent to generate Tc with a lower oxidation state. The product of the reaction between the metal ion and the peptide is a complex of the metal ion and the peptide. For example, the following structures could result from use of the invention, using Tc labeling of peptides containing metal-ion binding domains consisting of Cys and His groups as an example:

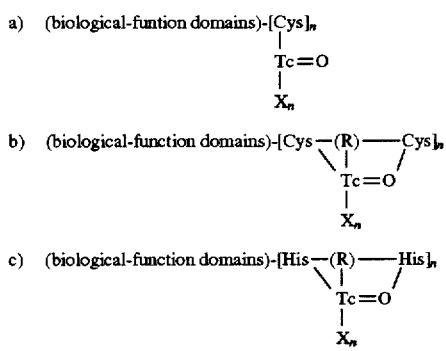

wherein R is an amino acid sequence containing from 1 to about 20 amino acids and $X_n$ is an anion, such as a halogen (e.g. fluoride or chloride), or a solvent molecule, such as water. In the foregoing, the biological-function domains are a peptide sequence including at least two or more linear repeat, linked or branched biologically active peptide sequences.

The resulting Tc-peptide bond should have a sufficiently high bond strength to minimize the exchange of the radionuclide to transferrin an serum albumin. The complex should be thermodynamically stable under varying physiological conditions and exhibit acceptable toxicological properties.

Most stannous reductions are performed at a pH of from about 5 to about 7. With amino acid side chains in a solution below pH 7, the basic amino acids are positively charged, the acidic amino acids are largely negatively charged, the alcoholic amino acids are neutral, and methionine is neutral. Since reduced technetium binds more readily to neutral hydrogen donors rather than positively charged hydrogen donors, at the pH range 5 to 7 only Cys and His are optimal $^{99m}$Tc binding site candidates. For both Cys and His, radiolabeling yields are dependant on pH, and are theoretically optimal at or near the $pK_a$.

In Zamora P. O. and Rhodes B. A., U.S. patent application Ser. No. 07/840,077, entitled *Peptide-Metal Ion Pharmaceutical Preparation and Method*, which application is incorporated herein by reference, the use of peptide-based metal-ion labeled compositions as pharmaceuticals is taught, together with methods of labeling peptides, proteins and other similar substances with radiometals, paramagnetic metals and other medically useful metal ions. This invention also teaches that peptides containing a biological-function domain and a medically useful metal ion-binding domain can be labeled with medically useful metal ions for use in diagnosis and treatment of a variety of pathologic conditions. Accordingly, the teachings of this application are incorporated herein by reference.

Metal-Ion Binding Domains.

The metal ion-binding domain of the peptide involves one or more amino acids containing sulfur, nitrogen or oxygen which is available for binding, or which can be made available for binding to metal ions. Commonly used amino acids include Cys, Pen and His, or any combination thereof. The simplest case takes the form $(R_1)-[Cys]_n-(R_2)$ wherein $[Cys]_n$ is the medically useful metal ion-binding domain and n is typically a number between 1 and about 6; and $R_1$ and $R_2$ are each an amino acid sequence containing from 0 to about 20 amino acids, with at least $R_1$ and $R_2$ including the biological-function domain. In this and all related forms, it should be noted that $R_1$ and $R_2$ are interchangeable; either can contain the biological-function domain, the biological-function domain may include part or all of both $R_1$ and $R_2$, and the biological-function domain may constitute only a portion of the amino acid sequence in either $R_1$ or $R_2$. The order of components for these purposes can be varied, so that $(R_1)-[Cys]_n-(R_2)$, $(R_2)-[Cys]_n-(R_1)$, $[Cys]_n-(R_2)-(R_1)$, $[Cys]_n-(R_1)-(R_2)$ and the mirror images of the last two orderings are all equivalent, even though the resulting peptides may significantly differ in other aspects.

Other forms of the same general configuration include $(R_1)-[Cys-(R_2)-Cys]_n-(R_3)$, $(R_1)-[Cys-(R_2)-Pen]_n-(R_3)$, $(R_1)-[His-(R_2)-Cys]_n-(R_3)$, $(R_1)-[His-(R_2)-Pen]_n-(R_3)$, and $(R_1)-[His-(R_2)-His]_n-(R_3)$ wherein the sequence [. . .]$_n$ is the medically useful metal ion-binding domain with n typically being a number between 1 and about 6; and $R_1$, $R_2$ and $R_3$ are each an amino acid sequence containing from 0 to about 20 amino acids, with at least one of $R_1$, $R_2$, and $R_3$ including the biological-function domain. Here too the ordering is irrelevant to the functional description; for example, $(R_3)-[His-(R_2)-Cys]_n-(R_1)$, $(R_1)-(R_3)-[His-(R_2)-Cys]_n$, $(R_3)-(R_1)-[His-(R_2)-Cys]_n$, mirror images of the foregoing two orderings, all orderings in which the positions of His and Cys are reversed, and orderings in which the biological-function domain is present in any of the three regions $R_1$, $R_2$ and $R_3$, any portion of the three regions $R_1$, $R_2$ and $R_3$, or any combination of the three regions $R_1$, $R_2$ and $R_3$, are all equivalent to the third configuration listed above, $(R_1)-[His-(R_2)-Cys]_n-(R_3)$. Each of the other foregoing configurations can be similarly described.

In one preferred embodiment of the method for labeling peptides of the configurations set forth above, the following method can be employed:

a) adding a source of positively-charged transition metal, most preferably a Sn (II) agent, to the peptide containing amino acids comprising sulfur, nitrogen or oxygen which is available for binding, or which can be made available for binding to metal ions, in an amount sufficient to allow the positively-charged transition metal to undergo a replacement reaction, thereby forming transition metal-containing and sulfur-, nitrogen- or oxygen-containing complexes, or some combination thereof, and, b) adding a medically useful metal ion whereby the metal ion displaces the transition metal in the transition metal-containing and sulfur-, nitrogen- or oxygen-containing complexes and the metal ion and peptide form metal ion-containing and sulfur-, nitrogen-, or oxygen-containing complexes.

The preferred transition metal is Sn (II); useful sources of Sn (II) include stannous tartrate, stannous glucoheptonate, stannous gluconate, stannous phosphonate, stannous chloride, and stannous fluoride. The selection of the source of Sn (II) and its final concentration depends on the intended medical application of the peptide, the nature of the peptide, the relative and absolute number of thiolate groups and the metal ion to be used. In one embodiment stannous tartrate is used at a concentration of 1.25 mM. The stannous tartrate is prepared in a buffer composed of 10 mM tartrate and 40 mM phthalate, pH 5.6, and is added to peptide to yield a final concentration of 1 mg/mL peptide solution.

Sn (II) can be stabilized by use of carboxylic acids, such as acetate, citrate, phthalate and tartrate. A wide range of dicarboxylic acids, known to those skilled in the art, may be similarly used to stabilize the Sn (II) and/or to act as a buffer. If the plithalate and tartrate are in molar excess relative to the Sn (II), then these dicarboxylic acids also stabilize the medically useful metal ion in a form which can react with the peptide. In one embodiment, tartrate and phthalate are used in the Sn (II) agent at concentrations of 10 mM and 40 mM, respectively.

Similarly, the Sn (II) and the medically useful metal ion may be stabilized by free aminio acids used singly or in combination with other agents. The type of amino acid used and the specific concentration depends on the nature of the peptide and its intended use. In one embodiment, glycine is used at a concentration of 0.1–10 mM, and in another, histidine is used at a concentration of 0. 1–10 mM. In yet another embodiment, trace amounts of thiol-containing agent, such as cysteine, may be added to stabilize the Sn (II) and the medically useful metal ion.

The peptide may be stored in bulk form or in unit dose form after addition of the Sn (II) or other transition metal. For example, in one embodiment the peptide is stored at –20° C. in vials after introduction of the Sn (II). Methods used in lyophilization of peptides are known to those skilled in the art. Either frozen or lyophilized preparations may be maintained for an indefinite period before labeling by the addition of the medically useful metal ion.

In both the frozen and lyophilized storage forms, excipients may be added to the peptide to minimize damage which can arise from ice-crystal formation or free-radical formation. The type of excipient and the concentration depends on the nature of the peptide and the intended use. In one embodiment, glycine and inositol are used as excipients in lyophilized preparations.

A typical lyophilized preparation made by the embodiments set forth above would, upon rehydration, contain 10 mM tartrate, 40 mM phthalate, 22 μg of Sn (II), 200 μg of peptide, 2 mg/mL of glycine, and 2 mg/mL of inositol. To label with a medically useful metal ion, a typical lyophilized preparation is hydrated by the addition of a solution containing 0.9% NaCl (U.S.P.) or water for injection (U.S.P.) and the medically useful metal ion. Alternatively, it is possible to hydrate the lyophilized preparation, and to add the metal ion in a subsequent step. If a frozen preparation is used, it is thawed and allowed to come to room temperature, and a solution containing the medically useful metal ion is then added. The nature and amount of the medically useful metal ion and the specific reaction conditions depend on the isotopic nature of the metal, and the intended medical application. In one embodiment, $^{99m}$Tc is added in the form of pertechnetate ion in a solution of 0.9% NaCl. The $^{99m}$Tc is typically incubated for up to 30 minutes to insure completion of the reaction with the peptide, after which the radio-labeled preparation can be directly used in medical applications. In another embodiment, the $^{99m}$Tc is reduced and complexed to a transfer agent such as glucoheptonate, tartrate or the like, and the reduced and complexed $^{99m}$Tc is then added to the peptide preparation and allowed to incubate, thereby allowing transfer of the $^{99m}$Tc to the peptide.

In the embodiment in which $^{99m}$Tc is used, the Sn (II) is present in the peptide-containing solution in sufficient excess to alter the oxidation state of the Tc ion such that it can bind to ionizable groups. Similar approaches may be used to lower the oxidation state of other medically useful metal ions for subsequent binding to ionizable groups. The type of the metal ion, its isotopic nature, and concentration would depend on the intended medical application.

It is also possible to construct a peptide wherein the peptide further contains a metal ion-binding domain including one or more disulfide bonds. In that case, it is necessary to first reduce the disulfide bond or bonds. In a preferred method, the following steps are employed:

a) incubating the peptide with a reducing agent to reduce some or all of the disulfide bonds to thiolate groups;

b) removing excess reducing agent from the peptide substrate containing thiolate groups;

c) adding a source of Sn (II) agent to the thiolate-containing peptide preparation in an amount sufficient to form Sn (II)-containing and sulfur-containing complexes; and, d) adding a medically useful metal ion whereby the metal ion displaces the Sn (II) in the Sn (II)-containing and sulfur-containing complexes and the metal ion and thiolate-containing peptide form metal ion-containing and sulfur-containing complexes.

The order of the steps may be altered, and the method will still produce metal ion-labeled peptides. Accordingly, the claims are not limited to the order of steps presented therein. Specifically, it is possible, and in some cases advantageous, to add the Sn (II) to form Sn (II)-containing and sulfur-containing complexes prior to removing excess reducing agent from the peptide substrate. In this way, oxidation of thiolate groups or reformation of disulfide bonds and other cross-linkages is immediately minimized.

Different configurations of peptides with one or more disulfide bonds are possible, and can be labeled as set forth herein. The most common example is the form

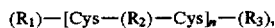

$(R_1)-[Cys-(R_2)-Cys]_n-(R_3)$, wherein $[Cys-(R_2)-Cys]_n$ is the medically useful metal ion-binding domain, which can appear in the amino acid sequence from 1 time to about 6 times; and $R_1$, $R_2$ and $R_3$ are each amino acid sequences containing from 0 to about 20 amino acids, with at least one of the amino acid sequences $R_1$, $R_2$ and $R_3$ comprising the biological-function domain. Other peptide configurations in which reducible disulfide bonds are present are also included in this method. These include the substitution of Pen for one or both Cys amino acids, as well as the modification of a native Met to allow it to form a disulfide bond. The biological-function domain can appear in any one of $R_1$, $R_2$ and $R_3$, and can also span more than one region, so that the biological-function domain may comprise, for example, $R_2$ and $R_3$, or some portion of $R_2$ and $R_3$. Any one or more of the regions $R_1$, $R_2$ and $R_3$ may contain no amino acids.

Numerous reducing agents have been described and are known to those skilled in the art. Particularly useful types of reducing agents include 2-mercaptoethanol; 1,4-dithiothreitol; 2,3-dihydroxybutane-1,4-ditillol; 2-aminoethanethiol HCl; thioglycolate; cysteine; reduced glutathione; Sn (II); Cu (I); and Ti (II). The reducing agent may be dissolved in a solute or may be attached to a solid phase. Reducing agents attached to a solid phase are commercially available, and methods for their use are known to those skilled in the art. The degree to which the peptide requires disulfide bond reduction depends on the nature of the peptide and its intended medical application. Generally speaking, milder reduction conditions and shorter incubation periods are normally employed than are required to reduce disulfide bonds in proteins or complex polypeptides, such as antibodies. In any event, reduction is halted before excessive fragmentation of the peptide or loss of the biological-function of the peptide occurs.

In one specific embodiment, Sn (II) is used as a reducing agent at a concentration of 5 mM. In this embodiment the Sn (II) is dissolved in a buffer composed of approximately 10 mM tartrate and 40 mM phthalate, pH 5.5, and the Sn (II) buffer admixed with a peptide substrate at a concentration of 8.3 mg/mL. The reduction reaction is allowed to proceed for a period of time at room temperature, three hours having been employed successfully with some peptides containing a single disulfide bond, after which time the reaction is terminated by removing excess Sn (II) ions by molecular sieve chromatography. One means of molecular sieve chromatography employs Sephadex G-25, with the chromatography gel pre-equilibrated, and the peptide eluted in 0.9% NaCl or other suitable buffer.

Removal of the reducing agent, whether Sn (II) or some other reducing agent, can be accomplished by a variety of suitable means, including such methods as dialysis, ultrafiltration, positive-pressure membrane filtration, precipitation, preparative high performance liquid chromatography, affinity chromatography, other forins of chromatography and preparative isoelectric focusing. Many of the reducing agents contain thiols, which if present in the final labeling mixture, can complex with the medically useful metal ion. Such complexes can have severe and unknown side effects if administered in vivo. Additionally, some reducing agents exhibit unacceptable toxicity. Thus removal of the reducing agent both limits the degree of reduction to that desired, as well as providing for increased utility and safety of the labeled preparation by removal of toxic or otherwise undesirable reducing agents.

Thiolate groups in reduced peptides are highly reactive and can interact to reform disulfide bonds. The use of Sn (II) is believed to minimize the reformation of disulfide bonds. Sources of Sn (II) include stannous tartrate, stannous glucoheptonate, chlornous gluconate, stannous phosphonate, stannous chloride, and stannous fluoride. The selection of the source of Sn (II) and its final concentration depends on the intended medical application of the peptide, the nature of the peptide, the relative and absolute number of thiolate groups and the metal ion to be used. In one embodiment stannous tartrate is used at a concentration of 1.25 mM. The stannous tartrate is added to the peptide after removal of the peptide-reducing agent. The stannous tartrate is prepared in a buffer composed of 10 mM tartrate and 40 mM phthalate, pH 5.6, and is added to peptide to yield a final concentration of 1 mg/mL peptide solution.

Other modified amino acid groups are also contemplated as metal ion-binding domains. These structures can be used particularly for binding $^{99m}$Tc for diagnostic imaging purposes, and isotopes of rhenium, including $^{188}$Re and $^{186}$Re for therapeutic purposes. Representative modified amino acid groups include the following:

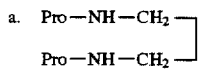

a.

b. Pro-Dap(Pro)-COOH
c. Pro-Gly-Gly-Gly (SEQ. ID NO. 3)
d. Pro-Gly-Cys
e. 3-(2-Thiazolyl)alanine substituted for Pro residues in a–d.
f. 2-Thiophenecarboxylic acid substituted for Pro residues in a–d.
g. 2-Thiopheneacetic acid substituted for Pro residues in a–d.
h. Gly-Cys(S-aminoethyl)
g. Cys(S-aminoethyl)-Cys(S-aminoethyl)

Both L and D amino acids could be used in a–g above. The Gly residue in a–g above could similarly be replaced by L- or D-Ala.

The foregoing modified amino acid groups can be prepared by solid phase or solution phase methods of peptide synthesis which are well known to those skilled in the art. The modified amino acid groups can be converted to active esters for covalent attachment to biological-function domains, or to other amino acid sequences in turn connected to or forming a part of biological-function domains. The foregoing modified amino acid groups could also be coupled using direct coupling approaches such as carbodiimide couplings and other such methods that are known in the art.

Peptides made using the modified amino acid sequences listed above may contain linear repeat, linked or branched biological-function domains. The biological-function domain may be any amino acid sequence which binds to specific cell surface receptors. In one embodiment, linear repeat, linked or branched $^{99m}$Tc-peptide labeling kits, containing any one of the modified amino acid sequences listed above, can be made. A typical lyophilized preparation would, upon rehydration, contain 200 µg of linear repeat, linked or branched peptide containing any one of the modified amino acid sequences listed above, 10 mM succinate, 0.5 mM EDTA and 0.4 mM stannous chloride, with a total tin content of 19 µg, and a kit pH of from 6.6 to 6.8. To label with $^{99m}$Tc, the lyophilized preparation is hydrated by the addition of a solution containing 400 µL of 0.9% NaCl or water and sodium pertechnetate. Alternatively, it is possible to hydrate the lyophilized preparation, and add the metal ion, such as $^{99m}$Tc, in a subsequent step. The peptide and $^{99m}$Tc is typically incubated for 30 minutes or longer, to insure completion of the reaction with the peptide, after which the radiolabeled preparation can be directly used in medical applications.

For therapeutic applications, the methods employed $^{99m}$Tc labeling of peptides set forth herein can be employed with $^{186}$Re or $^{188}$Re. However, the total concentration of Sn(II), to insure complete reduction of the perrhenate, may have to be increased, the incubation time may have to be increased, to insure sufficient radiochemical yields, and the incubation temperature may similarly be increased.

Chemotactic Peptides.

In one embodiment, a peptide is provided comprising at least two or more linked N-formyl-Met-Leu-Phe (N-formyl-MLF)(SEQ. ID NO. 2) sequences and a linked radiolabel, which peptide is useful for in vivo diagnostic applications, particularly for diagnostic imaging of infection, inflammation and other conditions characterized by accumulation of neutrophils. Preferably, the peptide comprises a biological-function domain comprising at least two or more linked N-formyl-MLF (SEQ. ID NO. 2)sequences and a metal-ion binding domain comprising metal ion binding sequences which can be coupled directly with metal ions. The peptides can be prepared in a format providing a labeling kit which can, in turn, be used to prepare a metal ion-peptide complex for in vivo use. It is also possible to provide for labeling of a peptide with the biological-function domain with a metal ion in vivo, such as through use of a peptide-avidin complex, which is injected in vivo, followed by a biotin-metal ion complex inject in vivo, resulting in formation of an in vivo peptide-avidin-biotin-metal ion complex. The peptides of this invention preferably contain:

a) at least two linked biological-function domains, each including at least one linked N-formyl-MLF (SEQ. ID NO. 2) sequence, and
b) one or more metal ion-binding domains which can complex with medically useful metal ions.

The biological-function domains of the chemotactic peptide include two or more linked peptide sequences which bind specifically to the cliemotactic receptors found on the cell surfaces of white blood cells and, in particular, neutrophils. The preferred peptide sequence is two or more linked N-formyl-MLF (SEQ. ID NO. 2) sequences, although other amino acids and amino acid sequences may be employed so long as they retain similar biological and molecular specificity. The peptide of this invention thus preferably includes the sequence N-formyl-MLF (SEQ. ID NO. 2), which may be repeated two or more times, a linking agent, and optionally amino acids in addition to N-formyl-MLF (SEQ. ID NO. 2). Usually, within the indicated sequences, there may be modifications, including deletions, insertions, substitutions, cyclations or use of amino acid mimics. For the most part, substitutions will be conservative, in which amino acids yielding substantially the same conformational and amphipathic characteristics may be employed. The peptides may use L-amino acids, or one or more of the amino acids may be substituted by D-amino acids (D-stereoisomer). In the alternative, tenninal amino acids may be employed having unnatural chirality. The peptide may also include a terminal amide or a terminal acylated amino acid, particularly acetylated or alkylated, particularly methylated, amino acids. Where a cysteine provides the metal-ion binding domain at the N-terminus, the cysteine may be S-alkylated or with an unsubstituted mercaptan group.

It is also possible to administer the peptide comprising two or more linked N-formyl-MLF (SEQ. ID NO. 2) sequences, and to perform the actual radiolabeling in vivo. This can be done, for example, using a biotin-avidin system, in which biotin is conjugated to the peptide, which is then injected into the patient. A radioisotope-labeled avidin complex is then injected, which binds to the peptide-biotin complex, forming a peptide-biotin-avidin-radiolabel complex, which can be detected by gamma scintigraphy or other detection means. This method presents certain advantages, in that maximum clearance and target binding parameters can be attained. To use this system, for example, it is possible to employ Biotin-HPDP (Pierce Chemical Co.), a cleavable, sulfhydryl-reactive biotinylation reagent. The peptide is dissolved in a 100 mM borate buffer pH 8.0 to a final concentration of 1 mg/mL, and biotin-HPDP at 1 mg/mL is added. The solution is mixed and incubated for 1 hour, and the biotinylated peptide separated from unconjugated materials by molecular sieve chromatography over Sephadex G-25. Avidin or strepavidin can be directly iodinated with $^{131}$I by standard methods. Alternatively, avidins can be conjugated to chelating agents such as DTPA or other agents which introduce thiols into the protein, and radiolabeled with $^{99m}$Tc. For use in vivo, the biotinylated peptide is injected intravenously and allowed to localize and clear from the general circulation, a time period generally of from 1 to 2 hours. Radiolabeled avidin is then injected; the radiolabeled avidin binds to the biotin, and consequently localizes at the disease lesion.

The N-formyl-MLF (SEQ. ID NO. 2) product may be used to monitor normal or abnormal metabolic events, to localize normal or abnormal tissues, to localize sites of disease, and to bind to blood constituents, including blood cells, and most preferably neutrophils, for subsequent localization of diseases, infections, and abnormal tissues. There is a wide variety of clinical conditions characterized by severe inflammation. Hidden, or occult, abscesses are particularly difficult to diagnose accurately. These lesions can be caused by a variety of bacteria and may be localized in any organ system. The location can be crucial to the choice of antibiotic or other therapy. Other significant conditions involving inflammatory foci include inflammatory bowel disease, appendicitis, opportunistic infections in patients with AIDS, and the inflammation associated with organ transplants and surgically implanted prostheses. Acute inflammatory disease may be life threatening; some types of abscesses have an overall mortality of 40%. Prompt diagnosis and treatment is crucial to patient survival.

The product can be used in a variety of medical procedures including gamma scintigraphy, specific photon emission computerized tomography (SPECT), positron emission tomography (PET), and magnetic resonance imaging(MRI). It is also possible to use the product to deliver a therapeutic quantity of radiation to a disease site. The medical application of the product of this invention depends on the type of peptide and the type of medically useful metal ion used.

The biological-function domain of the chemotactic peptide of this invention has substantially higher affinity than formylated peptides containing a single N-formyl-MLF (SEQ. ID NO. 2) sequence. The linked peptide sequence is:

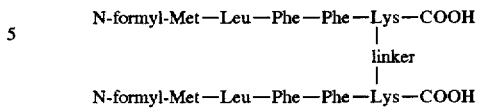

The linker portion is based on the use of a succinate as a bridge. The succinate can be introduced by use of succinic ONSu ester (solid phase) or by succinate-mediated fragment condensation with a water soluble diimide (solution phase), and results in the following structure, where NH is the epsilon amino group of Lys:

The metal ion-binding domain may be added to the carboxy-terminal end of the peptide. A variety of metal ion-binding domains may be employed; one preferred domain is the sequence Gly-His-Gly-Gly-Cys-OH (SEQ. ID NO. 4), which then provides the following composition:

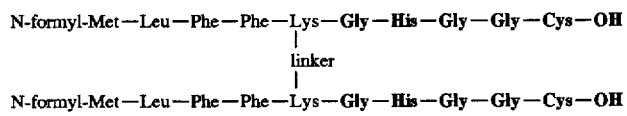

This composition is designed to retain an EC$_{50}$ at or near $6.1 \times 10^{-12}$ M and be able to bind a maximum of two $^{99m}$Tc molecules, thereby providing the highest specific activity possible. The peptide linkage through the lysine groups is designed to provide protease resistance at that site. To provide a higher degree of protease resistance, (D)-alanine can be introduced between Lys$^5$ and His$^6$ and the cysteine amidated to provide the compound:

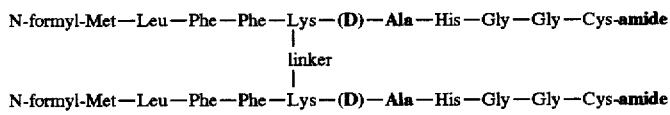

peptides containing a single N-formyl-MLF (SEQ. ID NO. 2) sequence. The linked peptide sequence, synthesized as a symmetric dimer without a metal-ion binding domain, has a 50% effective concentration (EC$_{50}$) of $6.1 \times 10^{-12}$M in the rabbit neutrophil lysosomal-enzyme-release assay. This EC$_{50}$ is approximately 100 fold higher in activity than Both this composition and its parent are designed to have a relatively high hydrophobic moment, and as a consequence to be cleared at least in part to the liver. To increase kidney clearance one glycine at the carboxy terminal end may be substituted with a glutamic acid to provide the following construction:

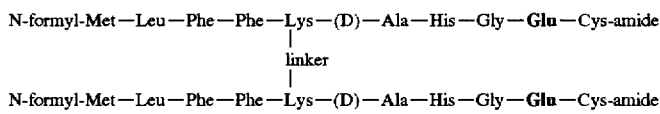

Peptides can be prepared, depending on the design, by either conventional solid-phase t-butyloxycarbonyl (t-Boc) or 9-fluoroenylmethyloxycarbonyl (Fmoc) protocols or classical solution phase (rapid mixed-anhydride) synthesis. Formylation can conveniently be accomplished by dicyclohexylcarbodiimide (DCC)/hydroylbenztriazole (HOBt) coupling of formic acid (solid phase) or by other methods known in the art. Interinediate deprotection can conveniently be accomplished by anhydrous trifluoroacetic acid (TFA) (Fmoc protocol), anhydrous hydrofluoric acid (t-Boc protocol) or catalytic hydrogenation (benzyl esters prepared by solution phase).

Thus, to construct a peptide of this invention, a synthesis scheme can be employed in which a t-Boc-Cys (p-MeOBzl) -resin is used with standard t-Boc chemistry to prepare the linear sequences. A tosyl (Tos) or benzyloxy methyl (Bom)

or other specific sequences added to improve clearance. A solid-phase strategy may be employed using either t-Boc-Orn (Fmoc) or t-Boc-Lys (Fmoc) resins as the starting material. In this method, one chain is built through the alpha amino group using conventional t-Boc chemistries. Subsequently, the Fmoc group is removed and a second chain, which may be identical or different, is constructed using conventional Fmoc chemistries. Formyl groups are introduced as formic acid using DCC/HOBy and the Cys and His side chains are protected with the MeOBzl and Tos or Bom groups, respectively. Cleavage and deprotection can be performed with anhydrous HF with purification by reverse phase HPLC.

Alternate peptide sequences include the following:

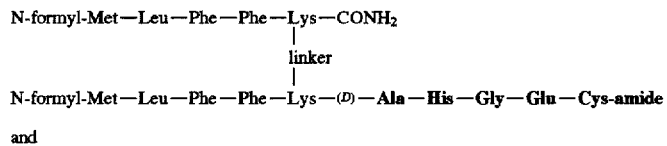

and

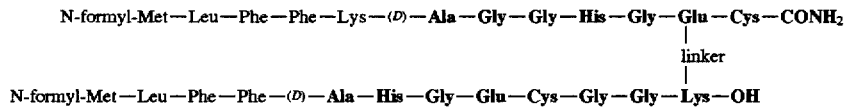

is used to protect the imidazole of histidine and Fmoc used to protect the epsilon-amino group of Lys. The formyl group is added by coupling of fornic acid using the same DCC/HOBt protocol as for the protected amino acids. Subsequently, the Fmoc group is removed in 20% piperidine in N-methyl-pyrrolidone, and two identical peptide chains coupled with succinic-N-hydroxysuccimide ester. The reaction is monitored using ninhydrin and, when complete, the peptide resin is treated with anhydrous HF to generate the desired peptide. The crude product is purified by HPLC.

A variety of linkers may be employed, in addition to dicarboxylic acids such as succinic-N-hydroxysuccimide ester. For example, the linker can be composed of diethyl amine, having the structural formula $H_2N—CH_2—CH_2—NH_2$, or other diamine compounds. The diamine compounds may be conjugated to peptides using carboxylated side chains of the peptide, such as terminal carboxyls, Gly, Asp, or combinations. Such a linker might be employed to construct a symmetric dimer having the following composition:

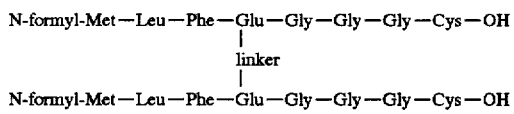

There are a number of homo- and hetero-bifunctional crosslinking agents which have been described, and are known to those skilled in the art. These agents may also be employed in this invention.

Asymmetric dimers are also provided in which, for example, the Cys residues are moved relative to each other, Use of D-amino acids is designed to confer resistance to protease degradation of the peptide. In these examples, use of only one $^{99m}$Tc-binding sequence is designed to minimize intramolecular crosslinking. The use of asymmetric $^{99m}$Tc-binding sequences also minimizes interchain crosslinking through the $^{99}$mTc.

In one embodiment, radiolabeling kits are made using the peptide sequences shown above. All steps are performed using aseptic technique, with all solutions purged with nitrogen, filtered through a 0.22 micron pore-size filter, and stored under a head-space gas of nitrogen. Any of the peptides shown above are dissolved in 10 mM/40 mM tartrate/phthalate buffer, pH 5.6, containing 0.9% NaCl to a concentration of 2 mg/mL. After dissolution, the peptide solutions are mixed 1:1 (v/v) with buffer containing 5 mM stannous tartrate. The solution is then incubated for 24 hours at room temperature. After incubation period, the solution is filtered through an ion exchange column (QMA-type, Millipore, Corp.) to remove spurious tin colloid and excess complexed tin ions. The peptide fraction is mixed 1:1 (v/v) with a buffer resulting in a final concentration of 10 mM tartrate/40 mM phthalate/0.6 mM stannous tartrate, at pH 5.6. Excipients, including lyophilization stabilizers, can also be introduced in this step. Glycine, inositol and other excipients serve to stabilize the proteins for subsequent lyophilization. After lyophilization, the kits can be radiolabeled with $^{99m}$Tc.

The kits are designed for direct radiolabeling, using stannous ions to reduce $^{99m}$Tc. To radiolabel, the lyophilized kits are rehydrated with 0.9% NaCl (U.S.P.), and after dissolution varying amounts of $^{99m}$Tc (sodium pertechnetate) added. During the radiolabeling, low amounts of stannous ions, present in excess, are used to reduce pertechnetate (Tc-VII) to a lower oxidation state (Tc-V). The reduced technetium is believed to undergo a replacement reaction with the peptide-bound tin ions, resulting in the proposed final $^{99m}$Tc-labeled complex illustrated below:

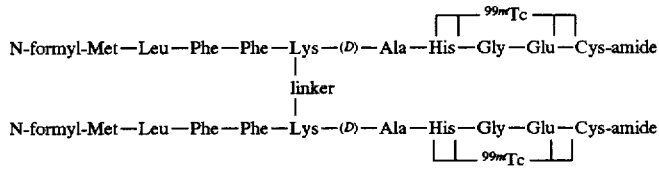

The excess tin ions site-protect any thiolates not directly involved in $^{99m}$Tc-binding.

YIGSR-Containing Peptides.

Peptides are also provided in which the biological-function domain is defined in the specification and claims as a sequence of the amino acids Tyr-Ile-Gly-Ser-Arg (SEQ. ID NO. 1) (YIGSR single amino acid code), and optionally amino acids in addition to YIGSR (SEQ. ID NO. 1). The peptide of this invention thus preferably includes the sequence YIGSR (SEQ. ID NO. 1), which is repeated one or more times. Usually, within the indicated sequences, there may be mutations, including deletions, insertions or substitutions. For the most part, substitutions will be conservative, in which amino acids having substantially the same conformation and polarity may be employed. The peptides may use L-amino acids, or one or more of the amino acids may be substituted by D-amino acids (D-stereoisomer). Particularly, one or more alanines may be substituted. In the alternative, terminal amino acids may be employed having unnatural chirality.

Examples of linear repeat peptide sequences included the sequence dCDGGGYdIGSRGGYdIGSRGGGDdC, in which the biological-function domains are the YIGSR (SEQ. ID NO. 1) sequences, and the metal ion-binding domains are dCDG and GddC (in this and subsequent examples, use of D-amino acids is indicated by a leading "d" in single code sequences, so that, for example, "dC" is (D)-Cys.). The peptide may be constructed to include a) a longer sequence to improve blood retention, b) repeated sequences of YIGSR (SEQ. ID NO. 1) to improve binding to platelets, and c) replacement of selected L-amino acids with D-amino acids to confer metabolic resistance. The following three peptide constructs (changes are shown as underlined) are examples of alternate peptide configurations:

The D-stereoisomer of aspartic acid is designed to increase protease resistance.

In this model, the space width between the two biologically active sites is increased by one amino acid, with the goal of increasing receptor access to each of the binding sites without steric hindrance.

In this model, a D configuration hydrophobic amino acid is introduced, with the goal of mimicking the hydrophobicity of the alkyl region of cysteine following the arginine as found in the parental laminin sequence. The goal is to increase radiometal bond strength while increasing protease resistance. All such peptides may be synthesized by solid-phase techniques using t-butyloxycarbonyl (Boc) protected amino acids, followed by reverse-phase HPLC purification.

In one embodiment, the peptide dCDGGGYdIGSRGGY-dIGSRGGGDdC is made into radiolabeling kits, with the final kits containing a total volume of 400 µL, and 200 µg of peptide, 2% maltose, 1.25 mM stannous tartrate, and a buffer consisting of 10 mM tartrate, 40 mM phthalate and 50 mM glycylglycine, at pH 6.6. To make the kits, the peptide is dissolved in nitrogen purged, stannous-free buffer containing 2% maltose to a final concentration of 1 mg/mL. This solution is then mixed 1:1 with the buffer containing 2.5 mM stannous tartrate, filtered through a 0.22 micron filter, and dispensed in 400 µL aliquots into 5 mL amber vials. All procedures are performed under nitrogen gas, and the vial headspace is nitrogen purged before stoppering and freezing at −70° C. To label with $^{99m}$Tc, the kits are thawed and allowed to come to room temperature, and a solution containing generator eluted sodium pertechnetate is added. The peptide and $^{99m}$Tc is typically incubated for 30 minutes or longer, to insure completion of the reaction with the peptide, after which the radiolabeled preparation can be directly used in medical applications.

YIGSR-containing peptides (SEQ. ID NO. 1), as well as peptides with different biological-function domains, can be made using a variety of branched peptide constructs, including constructs such as the following:

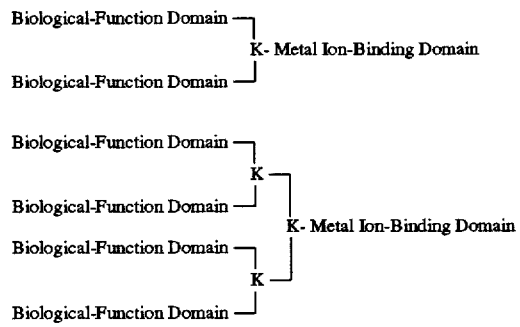

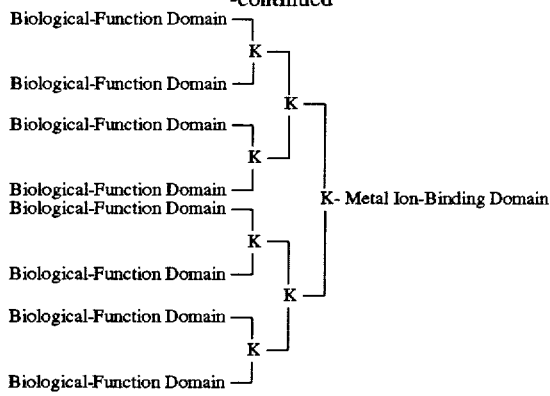

In which K is one or more amino acids forming a polyamide branch, such as lysine, which has two free amino groups and a carboxyl group. Lysine may be bound to the amino group of alanine or glycine through its carboxyl group, leaving both peptide bonds available for binding to biological-function domains, or to other lysine residues in the branching structure.

Using the foregoing branching system, peptides in the form of

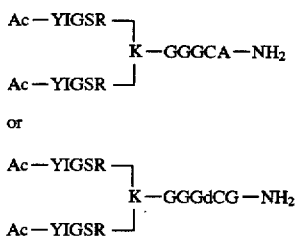

can readily be constructed, as well as similar configurations with four, eight or more branches. In the two foregoing examples, the sequences YIGSR (SEQ. ID NO. 1) are the biological-function domains, and the sequences GCA-NH$_2$ and GdCG-NH$_3$ include the metal ion-binding domains.

In one preferred embodiment, $^{99m}$Tc labeling kits can be made using the branched YIGSR (SEQ. ID NO. 1) peptides above. A typical lyophilized preparation would, upon rehydration, contain 200 μg of YIGSR (SEQ. ID NO. 1) branched peptide, 10 mM succinate, 0.5 mM EDTA and 0.4 mM stannous chloride, with a total tin content of 19 μg, and a kit pH of from 6.6 to 6.8. To label with $^{99m}$Tc, the lyophilized preparation is hydrated by the addition of a solution containing 400 μL of 0.9% NaCl or water and sodium pertechnetate. Alternatively, it is possible to hydrate the lyophilized preparation, and add the metal ion, such as $^{99m}$Tc, in a subsequent step. The peptide and $^{99m}$Tc is typically incubated for 30 minutes or longer, to insure completion of the reaction with the peptide, after which the radiolabeled preparation can be directly used in medical applications.

It is also feasible, and in some cases desirable, to make constructs which incorporate both linear repeat and branching or linking features. Thus, constructs such as the following are possible:

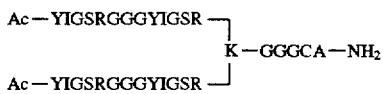

In this example, each branch contains two biological-function domains, each consisting of the sequence YIGSR (SEQ. ID NO. 1). A similar linked structure can also be constructed, such as:

It is also possible to construct peptides containing two different biological-function domains, which may, for example, be complimentary, or address related receptors on a molecule of interest.

The invention is further illustrated by the following non-limiting examples.

EXAMPLE 1

EVALUATION OF METAL-ION BINDING DOMAINS

To evaluate the effectiveness of different metal-ion binding domain peptide sequences, different sequences were evaluated using a peptide containing a single N-formyl-MLF (SEQ. ID NO. 2) sequence. Each peptide was dissolved to a final concentration of 2.0 mg/mL in chilled, nitrogen-purged 10 mM tartrate/40 mM phthalate buffer, pH 5.6 (P/T buffer) containing 2% maltose. The peptide solution was mixed (1:1) with P/T buffer containing 1.25 mM stannous tartrate. Aliquots (typically 0.25 mL containing 250 μg of peptide) were then sterile filtered through a 0.22 micron filter, and dispensed into individual vials. The head space of each vial was purged with nitrogen, the vials stoppered and crimped, and stored frozen at −70° C. For radiolabeling, the contents of a vial was allowed to come to room temperature and $^{99m}$Tc (sodium pertechnetate) added. After 30 minutes, the materials were used in experiments. In some cases, the buffer components were altered by the addition of glycylglycine so that the pH could be adjusted up to a high of pH 8.6.

To determine the relative amount of $^{99m}$Tc bound to a given peptide preparation, aliquots of the $^{99m}$Tc-labeled preparations were analyzed by molecular sieve HPLC, reverse phase chromatography, and instant thin layer chromatography.

The initial radiolabeling studies with histidine-containing peptides were conducted at a pH of 5.6, and binding was observed for all the peptides examined. The order of binding was essentially the same in all analytical systems used to assay binding, radiometric HPLC, ITLC (for unbound pertechnetate), and reverse phase chromatography. The relative percentage $^{99m}$Tc associated with the peptide, in decreasing order, is shown in Table 1.

TABLE 1

| PEPTIDE | % BINDING BY RADIO-HPLC |
| --- | --- |
| N-formyl-Met—Leu—Phe—Gly—Gly—His—Gly—Gly—Cys (Seq. ID NO. 5) | 89% |
| N-formyl-Met—Leu—Phe—Gly—His—Gly—Gly—His—Gly—His—Gly—Gly—His (Seq. ID. NO. 6) | 82% |
| N-formyl-Met—Leu—Phe—Gly—Gly—His—Glu—Lys—Gly—His—Gly—His—Trp (Seq. Id NO. 7) | 46% |
| N-formyl-Met—Leu—Phe—Gly—Gly—His—Trp (Seq. ID No. 8) | 42% |

ITLC was used to measure the amount of peptide-bound (and unbound) $^{99m}$Tc and the amount of radiolabeled aggregate/colloid. Both measurements involved the use of TLC-SG (Gelman Sciences, #61886) chromatography paper, cut into 1.5×10 cm strips and activated by heating for 30 minutes at 110° C., as per the manufacturer's instructions. Only small amounts of radiocolloid (less than 1%) were found in all of the preparations as determined by ITLC over albumin-coated ITLC strips and using a MeOH/ammonia/water solvent (2:1:5).

Radiometric molecular-sieve HPLC was performing using a 7.5×300 mm TSK G3000SW column preceded with a TSK-SW 7.5×75 mm guard column (TosoHaas, Philadelphia, Pa.) at a flow rate of 1 mL/minute phosphate buffered saline (0.01M phosphate, pH 7.0, containing 0.15 M NaCl), with a UV and radioisotope detector in series. Radiometric HPLC used in a molecular sieve mode revealed that all of the chemotactic peptides radiolabeled and eluted in a position which was distinct from that obtained with $^{99m}$Tc-pertechnetate.

EXAMPLE 2

EFFECT OF pH ON RADIOLABELING KITS

To evaluate the possibility that pH could contribute to an increase in labeling efficiency, the peptide:

N-formyl-Met-Leu-Phe-Gly-His-Gly-Gly-His-Gly-His-Gly-Gly-His  (SEQ. ID NO. 6)

was formulated in radiolabeling kits at pH values of 5.6, 6.6, 7.6, and 8.6. In these preparations, the buffer was composed of 20 mM citrate and 50 mM glycylglycine containing 0.6 mM stannous tartrate. The use of glycylglycine was found to keep the stannous ions in solution without the formation of colloid. In these studies the most effective pH for radiolabeling was found to be 7.6 as demonstrated using HPLC and confirmed by TLC using saline as a developer. At pH 5.6 doublet peaks were observed by HPLC analysis. The lead peak decreased noticeably at pH 6.6, was absent at pH 7.6, and reappeared at pH 8.6. In TLC studies using saline as a developer, the amount of radiolabel at the origin increased up to pH 7.6 and then fell dramatically, as is shown in Table 2 presented below.

TABLE 2

Effect on radiolabeling of varying the pH of radiolabeling kits of the peptide sequence
N-formyl-Met—Leu—Phe—Gly—His—Gly—Gly—His—Gly—His—Gly—Gly—His
(Seq. ID NO. 6)

| pH OF LABELING | TYPE OF HPLC PEAK | HPLC % RECOVERY | TLC % cpm AT ORIGIN | TLC % COLLOID |
| --- | --- | --- | --- | --- |
| 5.6 | doublet | 61.5 | 88.7 | 3.0 |
| 6.6 | doublet | 84.6 | 96.0 | 2.9 |
| 7.6 | singlet | 100.5 | 98.0 | 5.5 |
| 8.6 | doublet | 11.9 | 10.0 | 12.5 |

EXAMPLE 3

PREPARATION OF PEPTIDE CONTAINING TWO LINKED CHEMOTACTIC SEQUENCES

A peptide of the following configuration is synthesized using conventional means:

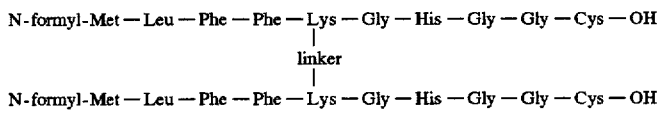

The peptide is solubilized in a buffer, allowed to incubate, and purified by ion exchange column chromatography, resulting in a peptide in a buffer composed of 10 mM tartrate, 40 mM phthalate, and 0.6 mM stannous tartrate, at pH 5.6. The peptide is radiolabeled by the addition of sodium pertechnetate $^{99m}$Tc.

EXAMPLE 4

USE OF PEPTIDE CONTAINING TWO LINKED CHEMOTACTIC SEQUENCES

A radiolabeled peptide containing two linked chemotactic sequences, such as the peptide of Example 3, is prepared. The preparation is injected into a patient suspected of having an internal infection or inflammation, and after a suitable period thereafter the patient is imaged using planar gamma scintigraphy.

EXAMPLE 5

SYNTHESIS OF PEPTIDE CONTAINING TWO ASYMMETRICAL LINKED CHEMOTACTIC SEQUENCES

A peptide of formula weight 1,756 was synthesized, with the following structure:

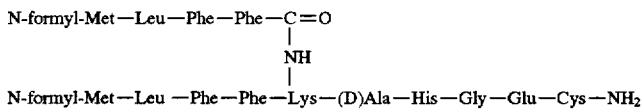

Using reverse phase HPLC, with a C18 column and linear gradient of 0.1% trifluoroacetic acid and 0.1% TFA in acetonitrile as solvents, the peptide eluted as a single peak.

EXAMPLE 6

PREPARATION OF A LINEAR PEPTIDE CONTAINING REPEAT YIGSR (SEQ. ID NO. 1) SEQUENCES

A peptide with a longer sequence to improve blood retention and with repeated sequences of YIGSR (SEQ. ID NO. 1) to improve binding to platelets was synthesized. Synthesis was done by solid-phase synthesis techniques using t-butyloxycarbonyl (Boc) protected amino acids added sequentially to a Cys-resin ester, followed by reverse-phase HPLC purification. The sequence of the peptide was as follows:

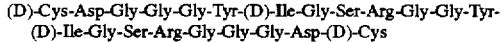

The dCDGGGYdIGSRGGYdIGSRGGGDdC peptide has a purity of greater than 98% as determined by reverse phase HPLC. The amino acid composition was confirmed by amino acid analysis.

The radiolabeling kit formulation included 200 µg of dCDGGGYdIGSRGGYdIGSRGGGDdC, in a tartrate/phthalate/glycylglycine buffer (10/25/40 mM), with 1.2 mM stannous tartrate, and was reconstituted to a 400 µL total volume. This peptide was evaluated using both column chromatography and thin-layer chromatography. Positive binding was over 90% with QMA, CM and $C_{18}$ columns, with less than 9% loss to the size exclusion column used for HPLC. Heat-treated ITLC-SG strips showed less than 5% free pertechnetate, with less than 2% colloid shown by albumin-coated ITLC-SG strips using an MeOH/NH$_4$OH/water solvent system.

In vitro studies were performed with $^{99m}$Tc-labeled dCDGGGYdIGSRGGYdIGSRGGGDdC using human whole blood clots and platelets. In these experiments, aliquots of 0.1 mL human blood were placed in inclined Petri dishes until the clot was well formed. The clots were rinsed three times with phosphate buffer, and 10 µCi of $^{99m}$Tc-dCDGGGYdIGSRGGYdIGSRGGGDdC added. After incubation at room temperature for one hour, clots were again washed three times, and residual activity measured. For platelet binding assays, platelets were harvested using routine methods and then incubated with $^{99m}$Tc-dCDGGGYdIGSRGGYdIGSRGGGDdC, washed and assayed. Up to 50 µg of $^{99m}$Tc-dCDGGGYdIGSRGGYdIGSRGGGDdC was used, with no change in the slope of the curve and with no apparent saturation of binding sites. Blocking experiments with cold dCDGGGYdIGSRGGYdIGSRGGGDdC showed that the $^{99}$mTc-dCDGGGYdIGSRGGYdIGSRGGGDdC binds specifically and selectively to clots and platelets as compared to control experiments using nonspecific human $^{99m}$Tc-IgG.

Animal biodistribution studies showed rapid blood clearance, urinary excretion and to a less degree GI tract excretion. $^{99m}$Tc-dCDGGGYdIGSRGGYdIGSRGGGDdC was lower in all organs except kidneys when compared to either nonspecific human $^{99m}$Tc-IgG or $^{99m}$Tc-CDPGYIGSR (derived from SEQ. ID NO. 1). This results in significantly lower background, with correspondingly higher target-to-non-target ratios. The $^{99m}$Tc-dCDGGGYdIGSRGGYdIGSRGGGDdC consistently visualized thrombi induced in rats within 30 minutes post injection. The in vivo scintigraphic (thrombus/contralateral side) ratio was 3:1, and the ex vivo direct counting (thrombosed to nonthrombosed vessel segment) ratio was 5.4:1.

EXAMPLE 7

PREPARATION AND LABELING OF A TWO BRANCHED PEPTIDE CONTAINING YIGSR (SEQ. ID NO. 1) SEQUENCES

A dimeric peptide of the following configuration was synthesized and purified:

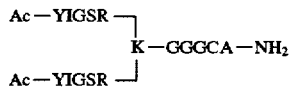

This peptide was examined by reverse phase HPLC, and was shown to elute as a single peak.

Radiolabeling kits were prepared, with each kit containing 200 µg of the branched YIGSR (SEQ. ID NO. 1) peptide; 1 mM SnCl$_2$; 1.1 mM EDTA; and 20 mM succinate buffer, at pH 6.6, in 400 µL total volume. The kits were prepared under nitrogen atmosphere, and dispensed in 3 mL amber colored serum vials. Both frozen and lyophilized kits were prepared, and both were stored at −20° C. until further use.

Both the lyophilized and the frozen kits were individually labeled with $^{99m}$Tc. For this purpose the frozen kit was thawed to room temperature and the lyophilized kit was first reconstituted with 400 µL of sterile water. 1–15 mCi of commercially available $^{99m}$Tc in the form of sodium pertechnetate contained in 200–1000 µL volume was added to both kits. Kits were allowed to incubate at room temperature for 30 minutes before testing. Labeling was tested by reverse phase HPLC and ITLC. These test results showed the following:

a. 90–95% of the total eluted radioactivity was associated with the peptide peak(s).

b. 3–7% of the radioactivity appeared in HPLC profiles as a distinct peak at the solvent front, presumptively representing unbound $^{99m}$Tc.

c. The peptide labeled as two distinct peaks, which were identified as the monomeric and dimeric peptide species. The dimeric species consists of two, two-branched peptides which are cross-linked.

The ratio of the monomer to dimer peaks ranged between 3:1 to 2.5:1.

e. The ratios of monomer to dimer peaks appeared to be related to length of incubation of the labeled peptide.

For example, after incubation for five hours at room temperature the ratio of monomeric to dimeric peaks was approximately 6:1 as measured by HPLC.

d. ITLC results indicated the presence of 3-7% free $^{99m}$Tc, confirming HPLC results, with a maximum of 3-5% $^{99m}$Tc colloid.

The strength of the $^{99m}$Tc-peptide bond was evaluated by cysteine challenge, in which the labeled peptide was incubated for 60 minutes at 37° C. with 10 mM Cys concentration. 62% of the $^{99m}$Tc remained bound to the peptide. The length of incubation prior to cysteine challenge appeared to affect the cysteine challenge results, with 77% of the $^{99m}$Tc remaining bound to the peptide when the peptide was incubated for approximately 5.33 hours prior to the cysteine challenge. It is hypothesized that the monomer species is relatively more stable to Cys challenge than the dimeric species. In addition, the monomeric species is thermodynamically more stable than the dimeric species, in that the dimeric species is being converted to the monomeric form over time.

EXAMPLE 8

PREPARATION AND LABELING OF AN EIGHT BRANCHED PEPTIDE CONTAINING YIGSR (SEQ. ID NO. 1) SEQUENCES

An eight branched peptide of the following configuration was synthesized and purified:

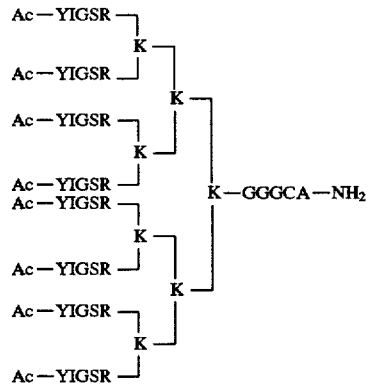

50 mg of this peptide, dissolved in 25 mL of water, was mixed with 25 mL of a nitrogen purged Sn-EDTA-Succinate buffer [ Sn(II)Cl$_2$ (1 mM), EDTA (1.1 mM), and succinic acid (20 mM), final pH 6.6.]. To this solution was added 10 mL (300 mCi) of $^{99m}$Tc in the form of sodium pertechnetate obtained from a technetium generator. After incubation at room temperature for 30 minutes, 12 mL was injected into a reverse phase HPLC column. The elution profile, monitored by radioactivity and UV, indicated that all the radioactivity was associated with the peptide peak, with a small (3% radioactivity) peak corresponding to a dimeric species of the peptide, with very little (<0.5%) free $^{99m}$Tc present, and up to 94% of injected radioactivity eluted from the column.

EXAMPLE 9

ALTERNATE BUFFER AND KIT FOR LINEAR PEPTIDE CONTAINING REPEAT YIGSR (SEQ. ID NO. 1) SEQUENCES

The peptide of Example 5, with the sequence dCDGGGYdIGSRGGYdIGSRGGGDdC, was labeled with 10 mCi of $^{99m}$Tc as sodium pertechnetate using the Sn-EDTA-succinate buffer of Example 7. The resulting product was monitored by reverse phase HPLC, with both UV and radioactivity flow cell monitors. The UV HPLC elution profile matched the radioactivity HPLC elution profile, with 7% of the $^{99m}$Tc unbound, and 89% of the $^{99m}$Tc bound to the peptide component. 90% of the injected radioactivity eluted from the column.

All of the foregoing are merely illustrative, and other equivalent embodiments are possible and contemplated.

Although the invention has been described with reference to these preferred embodiments, other embodiments can achieve the same results. Variations and modifications of the present invention will be obvious to those skilled in the art and it is intended to cover in the appended claims all such modifications and equivalents. The entire disclosures of all applications, patents, and publications cited above, and of the corresponding application, are hereby incorporated by reference.

What is claimed is:

1. A high affinity peptide-based pharmaceutical composition suitable for administration to a patient comprising:
   at least two linked amino acid sequence biological-function domains wherein the sequences are linked by means of peptide side chains; and
   one or more medically useful amino acid sequence metal ion-binding domains.

2. The peptide-based pharmaceutical composition of claim 1 wherein said peptide comprising at least two linked amino acid sequence biological-function domains and one or more medically useful metal ion-binding domains is selected from the group consisting of $(R_1)-[Y_1]_n-(R_2)$, $(R_1)-[Y_1-(R_2)-Y_1]_n-(R_3)$, and $(R_1)-[Y_1-(R_2)-Y_2]_n-(R_3)$ wherein,
   the medically useful metal ion-binding domain is selected from the group consisting of $[Y_1]_n$, $[Y_1-(R_2)-Y_1]_n$, and $[Y_1-(R_2)-Y_2]_n$ in which n is a number between 1 and about 6 and $Y_1$ and $Y_2$ are amino acids comprising a sulfur, nitrogen or oxygen which is available for binding to metal ions or can be made available for binding to metal ions;
   the linked amino acid sequence biological-function domains comprise at least one of the group consisting of $R_1$, $R_2$ and $R_3$; and
   those portions of $R_1$, $R_2$, and $R_3$ not comprising the biological-function domain each comprise an amino acid sequence containing from 0 to about 20 amino acids.

3. The peptide-based pharmaceutical composition of claim 2 wherein the medically useful metal ion-binding domain comprises at least one amino acid sequence consisting of at least one amino acid selected from the group consisting of cysteine, cystine, histidine, penicillamine, methionine, lysine, arginine, aspartic acid, glutamic acid and tyrosine.

4. The peptide-based pharmaceutical composition of claim 2 wherein said medically useful metal ion-binding domain is selected from the group consisting of $[Cys]_n$, $[Cys-(R_2)-Cys]_n$, $[Cys-(R_2)-Pen]_n$, $[His-(R_2)-Cys]_n$, $[His-(R_2)-Pen]_n$, $[His]_n$ and $[His-(R_2)-His]_n$ wherein,
   n is a number between 1 and about 6; and
   $R_2$ is an amino acid sequence containing from 1 to about 20 amino acids.

5. The peptide-based pharmaceutical composition of claim 2 wherein said medically useful metal ion-binding domain is selected from the group consisting of $$\left. \begin{array}{l} B-NH-CH_2- \\ B-NH-CH_2- \end{array} \right],$$

B-Dap(B)-COOH,

B-J-J-J,

B-J-Cys,

J-Cys(S-aminoethyl), and

Cys(S-aminoethyl)-Cys(S-aminoethyl)

wherein,
B is selected from the group consisting of Pro, 3-(2-Thiazolyl)alanine, 2-Thiophenecarboxylic acid, and 2-Thiopheneacetic acid;
"Dap" is 2,3 diaminopropionic acid;
J is selected from the group consisting of Gly and Ala residues; and
amino acids are L- or D-amino acids, or combinations thereof.

6. The peptide-based pharmaceutical composition of claim 1 wherein said linked biological-function domains comprise $$\begin{array}{c} \text{N-formyl-Met}-\text{Leu}-\text{Phe}-\text{Phe}-\text{Lys} \\ | \\ \text{linging agent} \\ | \\ \text{N-formyl-Met}-\text{Leu}-\text{Phe}-\text{Phe}-\text{Lys}- \end{array}.$$

7. The peptide-based pharmaceutical composition of claim 1 wherein said biological-function domains comprise (Tyr-Ile-Gly-Ser-Arg-U)$_n$,
wherein,
n is a number between 1 and about 8; and
U is an amino acid sequence containing from 1 to about 20 amino acids.

8. The peptide-based pharmaceutical composition of claim 1 wherein said biological-function domains comprise (Tyr-Ile-Gly-Ser-Arg-X)n, wherein,
n is a number between 1 and about 8; and
X is an amino acid sequence containing from 1 to about 20 amino acids which form a polyamide branch through peptide bonds joined to a central core molecule.

9. The peptide-based pharmaceutical composition of claim 1 wherein said composition further comprises a stannous metal ion labeling agent.

10. The peptide-based pharmaceutical composition of claim 9 wherein said composition further comprises a medically useful metal ion.

11. The peptide-based pharmaceutical composition of claim 10 wherein the medically useful metal ion is a radionuclide comprising an isotope selected from the group consisting of technetium, rhenium, indium, gold, silver, mercury and copper.

* * * * *

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: Peptide ( i i i ) HYPOTHETICAL: No ( i v ) ANTI-SENSE: No ( x i ) SEQUENCE DESCRIPTION: SEQ ID NO: 1:

```
    Tyr  Ile  Gly  Ser  Arg
    1                    5
```

( 2 ) INFORMATION FOR SEQ ID NO:2:

( i ) SEQUENCE CHARACTERISTICS:
        ( A ) LENGTH: 3 amino acids
        ( B ) TYPE: amino acid
        ( C ) STRANDEDNESS: single
        ( D ) TOPOLOGY: linear ( i i ) MOLECULE TYPE: Peptide ( i i i ) HYPOTHETICAL: No ( i v ) ANTI-SENSE: No ( i x ) FEATURE:
        ( D ) OTHER INFORMATION: Xaa is N- formyl-Met ( x i ) SEQUENCE DESCRIPTION: SEQ ID NO: 2:

```
    Xaa  Leu  Phe
    1
```

( 2 ) INFORMATION FOR SEQ ID NO:3:

( i ) SEQUENCE CHARACTERISTICS:
        ( A ) LENGTH: 4 amino acids
        ( B ) TYPE: amino acid
        ( C ) STRANDEDNESS: single
        ( D ) TOPOLOGY: linear ( i i ) MOLECULE TYPE: Peptide ( i i i ) HYPOTHETICAL: No ( i v ) ANTI-SENSE: No ( x i ) SEQUENCE DESCRIPTION: SEQ ID NO: 3:

```
    Pro  Gly  Gly  Gly
    1
```

( 2 ) INFORMATION FOR SEQ ID NO:4:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: Peptide ( i i i ) HYPOTHETICAL: No ( i v ) ANTI-SENSE: No ( x i ) SEQUENCE DESCRIPTION: SEQ ID NO: 4:

```
    Gly  His  Gly  Gly  Cys
    1                    5
```

( 2 ) INFORMATION FOR SEQ ID NO:5:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: Peptide ( i i i ) HYPOTHETICAL: No ( i v ) ANTI-SENSE: No ( i x ) FEATURE:
  ( D ) OTHER INFORMATION: Xaa is N- formyl-Met ( x i ) SEQUENCE DESCRIPTION: SEQ ID NO: 5:

```
Xaa  Leu  Phe  Gly  Gly  His  Gly  Gly  Cys
1                  5
```

( 2 ) INFORMATION FOR SEQ ID NO:6:

( i ) SEQUENCE CHARACTERISTICS:
    ( A ) LENGTH: 13 amino acids
    ( B ) TYPE: amino acid
    ( C ) STRANDEDNESS: single
    ( D ) TOPOLOGY: linear ( i i ) MOLECULE TYPE: Peptide ( i i i ) HYPOTHETICAL: No ( i v ) ANTI-SENSE: No ( i x ) FEATURE:
    ( D ) OTHER INFORMATION: Xaa is N- formyl-Met ( x i ) SEQUENCE DESCRIPTION: SEQ ID NO: 6:

```
Xaa  Leu  Phe  Gly  His  Gly  Gly  His  Gly  His  Gly  Gly  His
1                  5                            10
```

( 2 ) INFORMATION FOR SEQ ID NO:7:

( i ) SEQUENCE CHARACTERISTICS:
    ( A ) LENGTH: 13 amino acids
    ( B ) TYPE: amino acid
    ( C ) STRANDEDNESS: single
    ( D ) TOPOLOGY: linear ( i i ) MOLECULE TYPE: Peptide ( i i i ) HYPOTHETICAL: No ( i v ) ANTI-SENSE: No ( i x ) FEATURE:
    ( D ) OTHER INFORMATION: Xaa is N- formyl-Met ( x i ) SEQUENCE DESCRIPTION: SEQ ID NO: 7:

```
Xaa  Leu  Phe  Gly  Gly  His  Glu  Lys  Gly  His  Gly  His  Trp
1                  5                            10
```

( 2 ) INFORMATION FOR SEQ ID NO:8:

( i ) SEQUENCE CHARACTERISTICS:
    ( A ) LENGTH: 7 amino acids
    ( B ) TYPE: amino acid
    ( C ) STRANDEDNESS: single
    ( D ) TOPOLOGY: linear ( i i ) MOLECULE TYPE: Peptide ( i i i ) HYPOTHETICAL: No ( i v ) ANTI-SENSE: No ( i x ) FEATURE:
    ( D ) OTHER INFORMATION: Xaa is N- formyl-Met ( x i ) SEQUENCE DESCRIPTION: SEQ ID NO: 8:

```
Xaa  Leu  Phe  Gly  Gly  His  Trp
1                  5
```